(12) United States Patent
Barker et al.

(10) Patent No.: US 7,798,864 B2
(45) Date of Patent: Sep. 21, 2010

(54) LOW-PROFILE CONNECTOR FOR A NEUROSTIMULATION LEAD

(75) Inventors: John M. Barker, Ventura, CA (US);
Matthew B. Flowers, Irvine, CA (US);
Paul M. Meadows, Glendale, CA (US);
Randy L. Brase, Castaic, CA (US);
Robert Tong, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 12/402,007

(22) Filed: Mar. 11, 2009

(65) Prior Publication Data

US 2009/0233491 A1   Sep. 17, 2009

Related U.S. Application Data

(60) Provisional application No. 61/036,016, filed on Mar. 12, 2008.

(51) Int. Cl.
*H01R 24/04* (2006.01)
(52) U.S. Cl. ...................................... 439/668
(58) Field of Classification Search .................. 439/668
See application file for complete search history.

(56) References Cited

U.S. PATENT DOCUMENTS

| | | | |
|---|---|---|---|
| 3,757,789 A | 9/1973 | Shanker | |
| 3,908,668 A | 9/1975 | Bolduc | |
| 3,951,154 A | 4/1976 | Hartlaub | |
| 4,112,953 A | 9/1978 | Shanker et al. | |
| 4,180,078 A | 12/1979 | Anderson | |
| 4,245,642 A | 1/1981 | Skubitz et al. | |
| 4,259,962 A | 4/1981 | Peers-Trevarton | |
| 4,466,441 A | 8/1984 | Skubitz et al. | |
| 4,603,696 A | 8/1986 | Cross, Jr. et al. | |
| 4,715,380 A | 12/1987 | Harris | |
| 4,784,141 A | 11/1988 | Peers-Trevarton | |
| 4,860,750 A | 8/1989 | Frey et al. | |

(Continued)

OTHER PUBLICATIONS

PCT International Search Report for PCT/US2009/036788, Applicant: Boston Scientific Neuromodulation Corporation, Form PCT/ISA/210 and 220, dated Jun. 8, 2009 (6 pages).

(Continued)

*Primary Examiner*—Truc T Nguyen
(74) *Attorney, Agent, or Firm*—Vista IP Law Group LLP

(57) ABSTRACT

An implantable connector, implantable lead assemblies, and implantable lead assembly kits are provided. The connector comprises an electrically insulative receptacle having a port configured for receiving an electrical lead body portion that carries an electrical terminal, and an electrical spring clip contact mounted within the receptacle. The electrical contact includes a collar and opposing lever arms. The collar is configured for being placed between an expanded state for receiving the terminal therein when the lead body portion is received within the port, and a collapsed state to firmly engage the terminal. The opposing lever arms are configured for being displaced using a tool to correspondingly place the collar between the expanded state and the collapsed state. The implantable connector can be incorporated into a lead and used to receive another lead to form the lead assembly. A tool can be provided with the connector to provide the lead assembly kit.

39 Claims, 19 Drawing Sheets

U.S. PATENT DOCUMENTS

| | | | |
|---|---|---|---|
| 4,898,173 A * | 2/1990 | Daglow et al. | 607/37 |
| 4,899,753 A | 2/1990 | Inoue et al. | |
| 4,951,687 A | 8/1990 | Ufford et al. | |
| 4,995,389 A | 2/1991 | Harris | |
| 5,007,864 A | 4/1991 | Stutz, Jr. | |
| 5,201,865 A | 4/1993 | Kuehn | |
| 5,252,090 A | 10/1993 | Giurtino et al. | |
| 5,330,521 A | 7/1994 | Cohen | |
| 5,336,246 A | 8/1994 | Dantanarayana | |
| 5,383,913 A | 1/1995 | Schiff | |
| 5,413,595 A | 5/1995 | Stutz, Jr. | |
| 5,486,202 A | 1/1996 | Bradshaw | |
| 5,489,225 A | 2/1996 | Julian | |
| 5,509,928 A | 4/1996 | Acken | |
| 5,534,019 A | 7/1996 | Paspa | |
| 5,545,188 A | 8/1996 | Bradshaw et al. | |
| 5,545,189 A | 8/1996 | Fayram | |
| 5,582,180 A | 12/1996 | Manset et al. | |
| 5,679,026 A | 10/1997 | Fain et al. | |
| 5,720,631 A | 2/1998 | Carson et al. | |
| 5,782,892 A | 7/1998 | Castle et al. | |
| 5,796,044 A | 8/1998 | Cobian et al. | |
| 5,807,144 A | 9/1998 | Sivard | |
| 5,837,006 A | 11/1998 | Ocel et al. | |
| 5,843,141 A | 12/1998 | Bischoff et al. | |
| 5,931,861 A | 8/1999 | Werner et al. | |
| 6,038,479 A | 3/2000 | Werner et al. | |
| 6,038,481 A | 3/2000 | Werner et al. | |
| 6,080,188 A | 6/2000 | Rowley et al. | |
| 6,154,678 A | 11/2000 | Lauro | |
| 6,167,314 A | 12/2000 | Fischer et al. | |
| 6,192,278 B1 | 2/2001 | Werner et al. | |
| 6,343,233 B1 | 1/2002 | Werner et al. | |
| 6,397,108 B1 | 5/2002 | Camps et al. | |
| 6,428,368 B1 | 8/2002 | Hawkins et al. | |
| 6,466,824 B1 | 10/2002 | Struble | |
| 6,662,035 B2 | 12/2003 | Sochor | |
| 6,671,553 B1 | 12/2003 | Helland et al. | |
| 6,741,892 B1 | 5/2004 | Meadows et al. | |
| 6,799,991 B2 | 10/2004 | Williams et al. | |
| 6,805,675 B1 | 10/2004 | Gardeski et al. | |
| 6,854,994 B2 | 2/2005 | Stein et al. | |
| 6,895,276 B2 | 5/2005 | Kast et al. | |
| 6,968,235 B2 | 11/2005 | Belden et al. | |
| 7,083,474 B1 * | 8/2006 | Fleck et al. | 439/668 |
| 7,128,600 B2 | 10/2006 | Osypka | |
| 7,130,699 B2 | 10/2006 | Huff et al. | |
| 7,155,283 B2 | 12/2006 | Ries et al. | |
| 7,168,165 B2 | 1/2007 | Calzada et al. | |
| 7,231,253 B2 | 6/2007 | Tidemand et al. | |
| 7,241,180 B1 | 7/2007 | Rentas Torres | |
| 7,244,150 B1 | 7/2007 | Brase et al. | |
| 7,270,568 B2 | 9/2007 | Osypka | |
| 7,283,878 B2 | 10/2007 | Brostrom et al. | |
| 7,287,995 B2 | 10/2007 | Stein et al. | |
| 7,396,335 B2 | 7/2008 | Gardeski et al. | |
| 7,402,083 B2 | 7/2008 | Kast et al. | |
| 7,512,446 B2 | 3/2009 | Honeck | |
| 7,516,447 B2 | 3/2009 | Drew | |
| 7,526,339 B2 | 4/2009 | Lahti et al. | |
| 7,539,542 B1 | 5/2009 | Malinowski | |
| 7,548,788 B2 | 6/2009 | Chinn et al. | |
| 2006/0247749 A1 | 11/2006 | Colvin | |
| 2007/0142889 A1 | 6/2007 | Whitehurst et al. | |
| 2007/0150036 A1 | 6/2007 | Anderson | |
| 2007/0161294 A1 | 7/2007 | Brase et al. | |
| 2007/0168004 A1 | 7/2007 | Walter | |
| 2007/0168007 A1 | 7/2007 | Kuzma et al. | |

OTHER PUBLICATIONS

PCT Written Opinion of the International Search Authority for PCT/US2009/036788, Applicant: Boston Scientific Neuromodulation Corporation, Form PCT/ISA/237, dated Jun. 8, 2009 (6 pages).

* cited by examiner

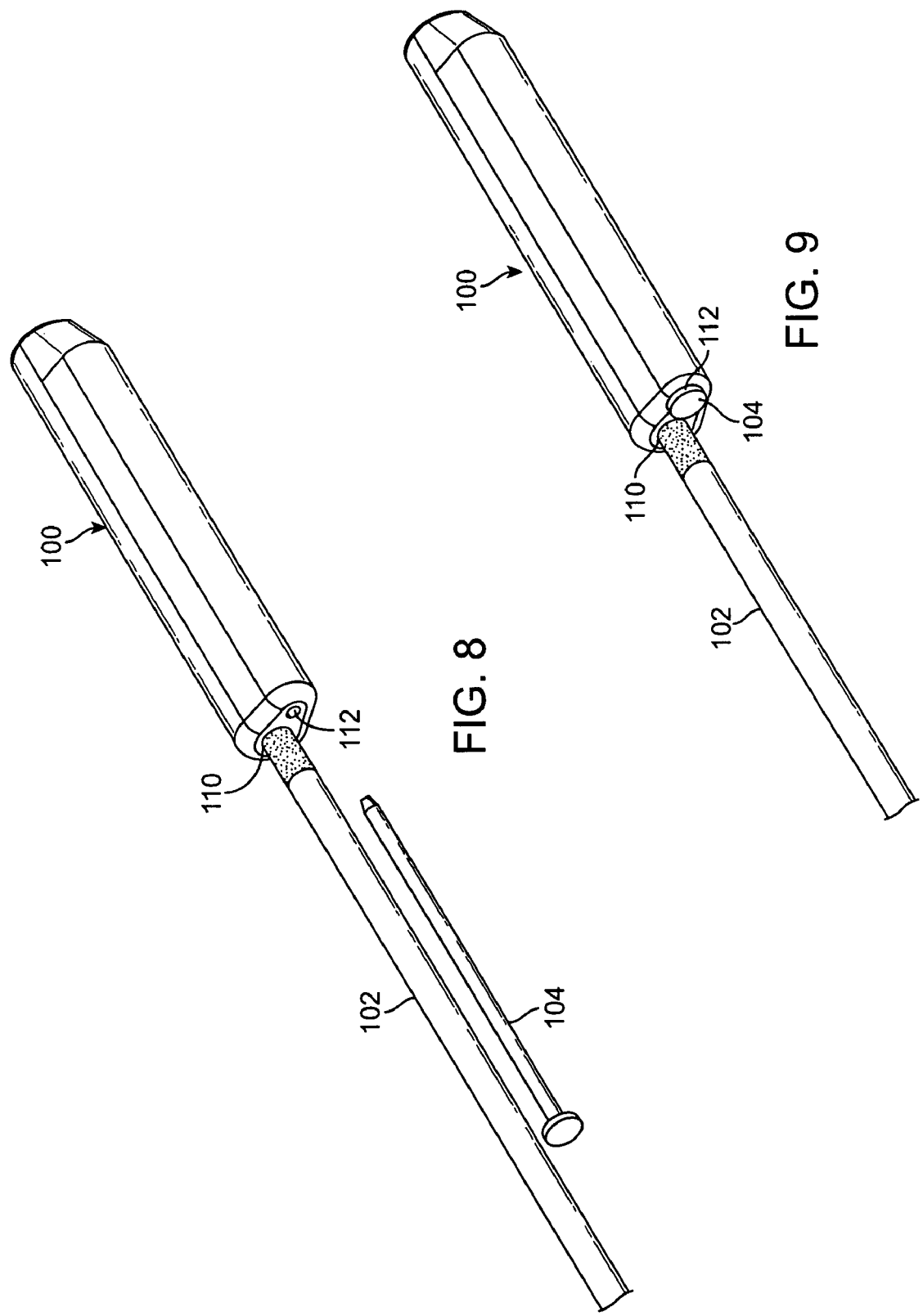

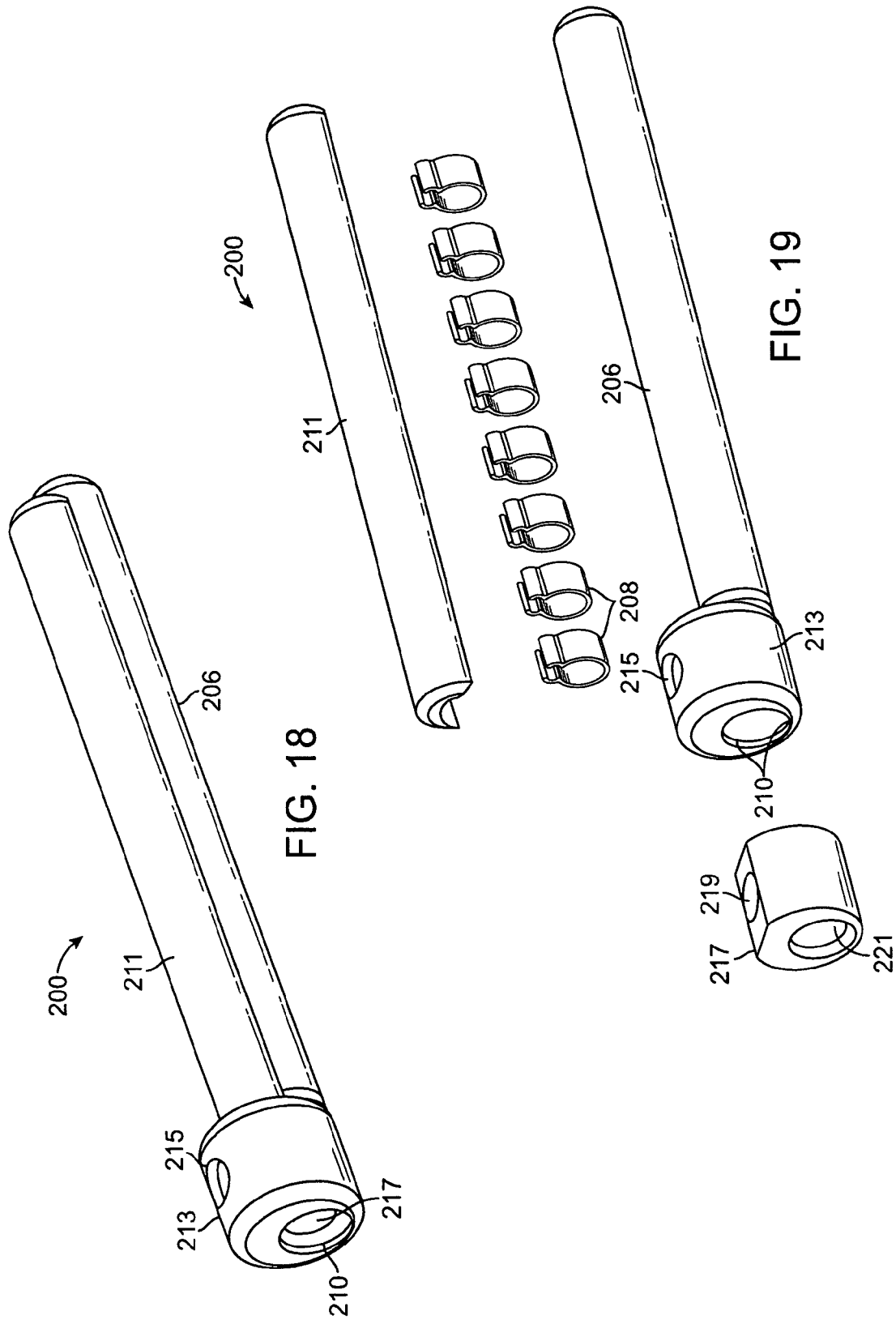

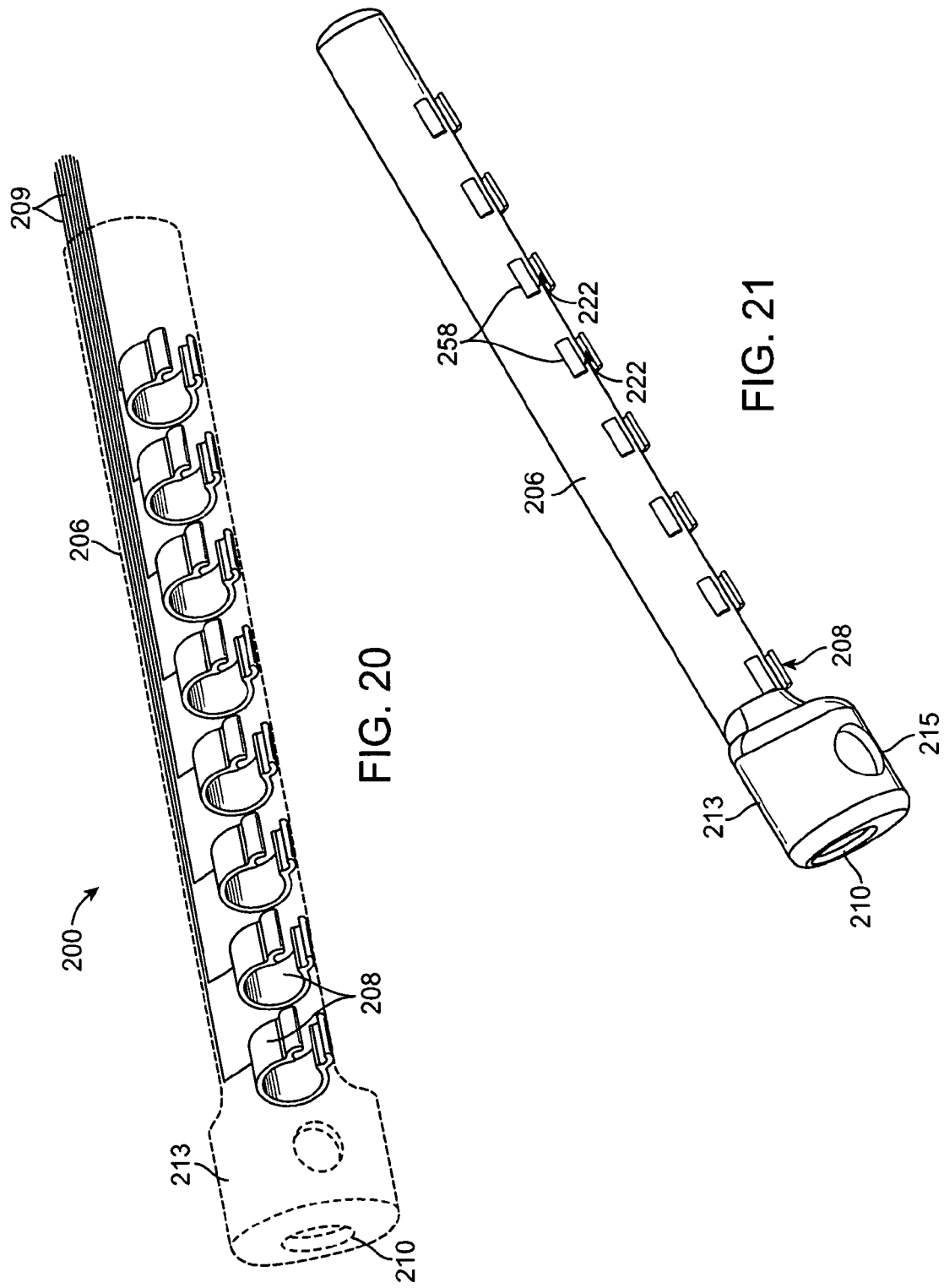

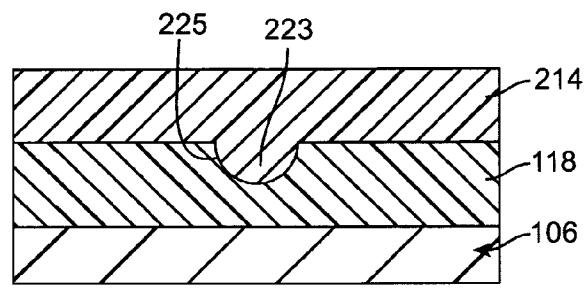
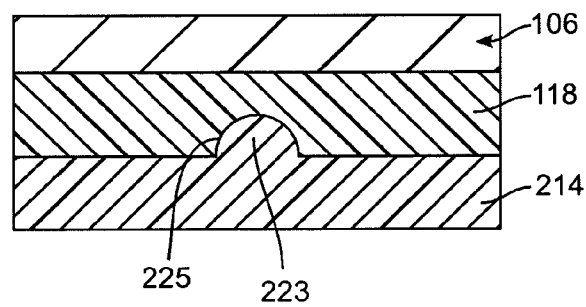
FIG. 24
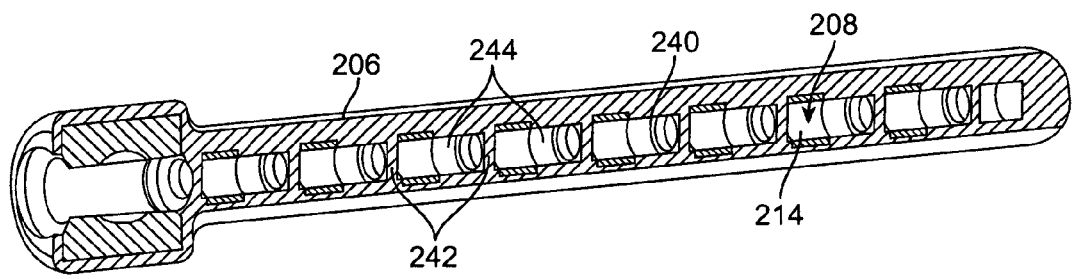
FIG. 25

LOW-PROFILE CONNECTOR FOR A NEUROSTIMULATION LEAD

RELATED APPLICATION

The present application claims the benefit under 35 U.S.C. §119 to U.S. provisional patent application Ser. No. 61/036,016, filed Mar. 12, 2008. The foregoing application is hereby incorporated by reference into the present application in its entirety.

FIELD OF THE INVENTION

The present invention relates to tissue stimulation systems, and more particularly, to connectors for coupling neurostimulation leads to implantable neurostimulators, extension leads, and adapters.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more stimulation leads implanted at the desired stimulation site and an implantable neurostimulator, such as an implantable pulse generator (IPG), implanted remotely from the stimulation site, but coupled either directly to the stimulation leads or indirectly to the stimulation leads via one or more extension leads in cases where the length of the stimulation leads is insufficient to reach the IPG. In some cases, the extension leads may be used to facilitate coupling of the neurostimulator, which may otherwise be incompatible with the stimulation leads or extension leads, thereto. Thus, electrical pulses can be delivered from the neurostimulator to the stimulation leads to stimulate the tissue and provide the desired efficacious therapy to the patient.

If the stimulation leads are to be directly connected to the neurostimulator, the proximal ends of the stimulation leads can be inserted into a connector of the neurostimulator, such that the terminals located at the proximal ends of the stimulation leads are coupled to corresponding electrical contacts within the connector. Individual wires are routed though each stimulation lead to connect the proximally-located terminals with the distally-located electrodes.

If the stimulation leads are to be indirectly connected to the neurostimulator via the extension leads, the proximal ends of the stimulation leads can be inserted into connectors located at the distal ends of the respective extension leads, such that the terminals of the stimulation leads are coupled to corresponding electrical contacts within the connectors of the extension leads. The proximal ends of the extension leads can then be inserted into the connector of the neurostimulator, such that terminals located at the proximal ends of the extension leads are coupled to the corresponding electrical contacts within the connector of the neurostimulator. Individual wires are routed though each extension lead to respectively couple the proximally-located terminals to the distally-located electrical contacts.

In the context of an SCS procedure, one or more stimulation leads are introduced through the patient's back into the epidural space under fluoroscopy, such that the electrodes carried by the leads are arranged in a desired pattern and spacing to create an electrode array. The specific procedure used to implant the stimulation leads will ultimately depend on the type of stimulation leads used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. In many cases, a stylet, such as a metallic wire, is inserted into a lumen running through the center of each of the percutaneous leads to aid in insertion of the lead through the needle and into the epidural space. The stylet gives the lead rigidity during positioning, and once the lead is positioned, the stylet can be removed after which the lead becomes flaccid.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

After proper placement of the stimulation leads at the target area of the spinal cord, the leads are anchored in place at an exit site to prevent movement of the stimulation leads. To facilitate the location of the neurostimulator away from the exit point of the stimulation leads, extension leads are sometimes used. In particular, the proximal ends of the stimulation leads, which include terminals respectively coupled to the electrodes on the stimulation leads, are inserted into connectors located at the distal ends of extension leads.

The proximal ends of the stimulation leads exiting the spinal column, or alternatively extension leads, are passed through a tunnel subcutaneously formed along the torso of the patient to a subcutaneous pocket (typically made in the patient's abdominal or buttock area) where a neurostimulator is implanted. The subcutaneous tunnel can be formed using a tunneling tool over which a tunneling straw may be threaded. The tunneling tool can be removed, the stimulation leads threaded through the tunneling straw, and then the tunneling straw removed from the tunnel while maintaining the stimulation leads in place within the tunnel.

The stimulation leads are then connected to the neurostimulator, which can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient. During the surgical procedure, the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. Any incisions are then closed to fully implant the system.

After the system is fully implanted, it is important that the subcutaneously implanted components, such as the neurostimulator and extension leads, be of a low-profile nature for aesthetic reasons as well as to prevent or minimize any discomfort of the patient that may otherwise occur by having rigid objects that do not conform to the natural curvature and movement of the patient.

However, in order to accommodate the present-day contacts, which either take the form of metal collars containing set screws or contacts or biasing mechanisms that frictionally engage the lead as it is introduced into the connector, the connectors of the extension lead and adapter are typically larger and stiffer than the bodies of the extension lead and adapter, thereby increasing the overall profile, while decreasing the conformity, of the extension lead and adapter.

In addition, in order to firmly secure the terminals of a lead within a connector (e.g., the terminals of the stimulation lead within the connector of an extension lead or neurostimulator, or the terminals of the extension lead within the connector of the neurostimulator), a special tool, such as a relatively expensive torque wrench, is typically used to tighten (within a predetermined tolerance range) at least one set screw that is either associated with each of the contacts or one end of the connector. The requirement of tools outside of the surgeon's normal practice increases the likelihood of their incorrect use with the lead system as well as increasing the time required to correctly complete the implantation procedure. These factors may decrease the effectiveness of the therapy or increase the possibility of patient injury.

Additionally, problems associated with maintaining sufficient electrical coupling between the contacts of the connector and the terminals of the lead can result in intermittent or failed connection to the lead, resulting in a failure in the intended therapy. Also, the use of set screws may mar the surface properties of the contacts rendering the entire implanted system at risk of complete removal. Furthermore, contacts that utilize biased friction mechanisms as an alternative to set screws may have relatively high insertion forces that prevent frictionless insertion of the lead into the connector, which may limit the number of lead insertions and withdrawals for the connector head or result in the clinician damaging the lead during its insertion into the connector. These contacts may also be relatively expensive, which given the number of contacts required, may result in a connector that is prohibitively expensive There, thus, remains a need for an improved connector for an electrical lead assembly.

SUMMARY OF THE INVENTION

In accordance with a first aspect of the present inventions, an implantable connector is provided. The connector comprises an electrically insulative receptacle having a port configured for receiving an electrical lead body portion that carries an electrical terminal, and an electrical spring clip contact mounted within the receptacle. In one embodiment, the connector further comprises an electrical conductor connected to the contact. The electrical contact includes a collar and opposing lever arms. The collar is configured for being placed between an expanded state for receiving the terminal therein when the lead body portion is received within the port, and a collapsed state to firmly engage the terminal. In one embodiment, the contact has a spring force that urges the collar into the expanded state. In another embodiment, the contact has a spring force that urges the collar into the collapsed state.

The opposing lever arms are configured for being displaced using a tool to correspondingly place the collar between the expanded state and the collapsed state. For example, the lever arms may be configured for being displaced toward each other to correspondingly place the collar in the expanded state and for being displaced away each other to correspondingly place the collar in the collapsed state. Or, the lever arms may be configured for being displaced away from each other to correspondingly place the collar in the expanded state and for being displaced toward each other to correspondingly place the collar in the collapsed state.

In one embodiment, the electrical contact comprises a sheet of metal having first and second opposing edges. A first one of the lever arms extends from the first edge, and a second one of the lever arms extends from the second edge. The sheet of metal is wrapped around on itself, such that the lever arms oppose each other. In another embodiment, the lever arms are axially offset from each other. In this case, the plurality of lever arms may comprise two lever arms and a single lever arm opposing and axially interposed between the two lever arms. In another embodiment, the receptacle has another port configured for receiving the tool. In still another embodiment, the lever arms are exposed outside of the receptacle, in which case, the connector may further comprise an electrically insulative cover configured for being interference fit over the lever arms.

The port may be further configured for receiving an electrical lead body portion that carries a plurality of electrical terminals axially spaced along the electrical lead body portion, and the implantable connector comprises a plurality of electrical spring clip contacts axially mounted within the receptacle, with each of the contacts including a collar and opposing lever arms. In this case, the collars are configured for being placed between an expanded state for receiving the respective terminals therein when the electrical lead body portion is received within the port of the receptacle and a collapsed state for firmly engaging the respective terminals, and the lever arms configured for being displaced using a tool to correspondingly place the collars between the expanded state and the collapsed state.

In accordance with a second aspect of the present inventions, an implantable lead assembly is provided. The lead assembly comprises a first electrical lead having a first lead body portion and an electrical terminal carried by the first lead body portion, and a second electrical lead having second lead body portion and a connector carried by the second lead body portion. The details of the electrical lead and connector may be the same as those described above. In one embodiment, the first lead body portion is a proximal lead body portion, and the first electrical lead further comprises a distal lead body portion and an electrode carried by the distal lead body portion. If an electrical conductor is connected to the contact, it can further extend through the second electrical lead. In the same manner described above, the first electrical lead has a plurality of electrical terminals axially spaced along the first lead body portion, in which case, the connector may comprise a plurality of electrical spring clip contacts axially mounted within the receptacle.

In accordance with a third aspect of the present inventions, an implantable lead assembly kit is provided. The lead assembly kit comprises an electrical lead comprising a lead body portion and an electrical terminal carried by the lead body portion, a tool, and a connector. The details of the electrical lead and connector may be the same as those described above. In one embodiment, the tool comprises a pin configured for being inserted between the lever arms to displace the lever arms away from each other. In another embodiment, the tool comprises a pair of tool arms configured for being placed between a closed state and inserted between the lever arms, and an open state to displace the lever arms away from each other. In the same manner described above, the electrical lead has a plurality of electrical terminals axially spaced along the first lead body portion, in which case, the connector may comprise a plurality of electrical spring clip contacts axially mounted within the receptacle.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a perspective view of the connector of FIG. 7, particularly showing the stimulation lead inserted into the connector and the pin external to the connector;

FIG. 9 is a perspective view of the connector of FIG. 7, particularly showing both the stimulation lead and pin inserted into the connector;

FIG. 18 is a perspective view of another embodiment of a connector that can be used in the tissue stimulation system of FIG. 1;

FIG. 19 is an exploded view of the connector of FIG. 18;

FIG. 20 is a perspective view of the connector of FIG. 18, particularly showing a receptacle of the connector in phantom;

FIG. 21 is a perspective view of the connector of FIG. 18, particularly showing a seal cover removed from the connector;

FIG. 24 is a cross-sectional view of the electrical contact of FIG. 22, particularly taken along the axis of the electrical contact;

FIG. 25 is a cross-sectional perspective view of the connector of FIG. 18, particularly taken along the axis of the connector;

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
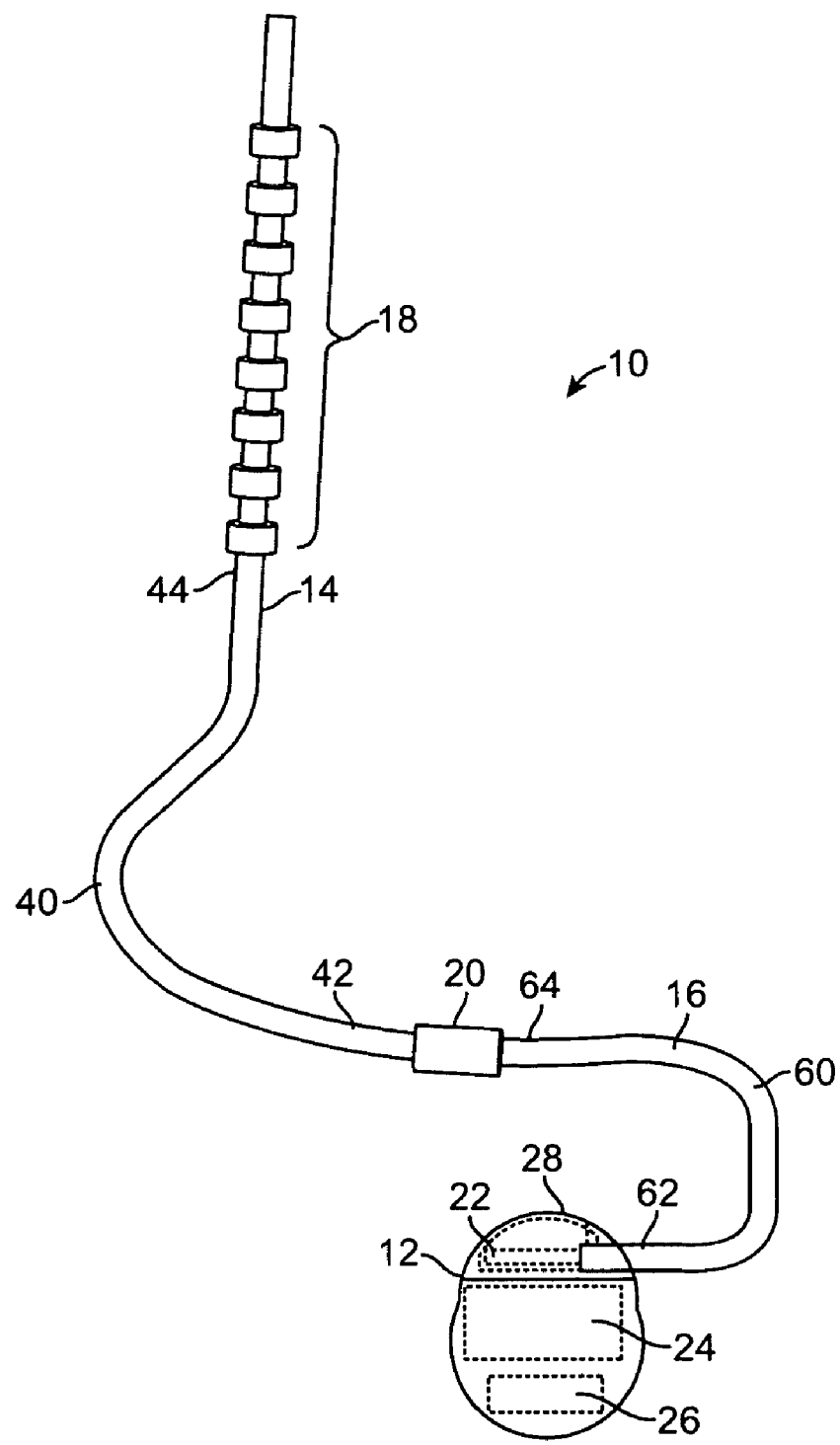
FIG. 1 is plan view of one embodiment of a tissue stimulation system arranged in accordance with the present inventions.
Figure 2:
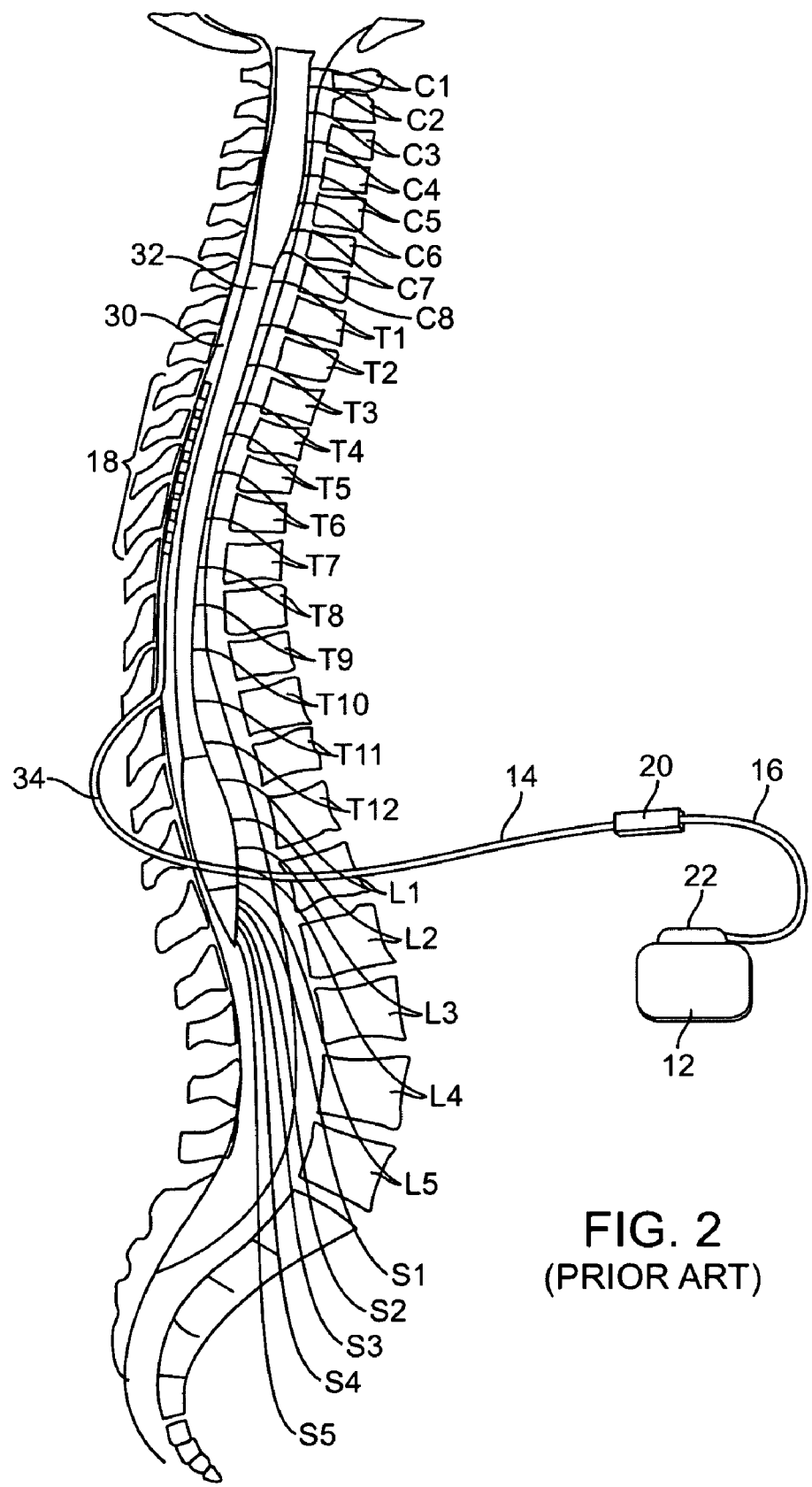
FIG. 2 is a plan view of the tissue stimulation system of FIG. 1 in use with a patient.

Referring first to FIGS. 1 and 2, a generalized tissue stimulation system 10 that may be used in spinal cord stimulation (SCS), as well as other stimulation applications, will be described. The stimulation system 10 generally comprises an implantable control module 12, an implantable stimulation lead 14, which carries an array of electrodes 18 (shown exaggerated for purposes of illustration), and an implantable extension lead 16. Although only one stimulation lead 14 is shown, more than one stimulation lead, and typically two stimulation leads, can be used in the stimulation system 10. As there shown, the proximal end of the stimulation lead 14 is removably mated to the distal end of the extension lead 16 via a connector 20 associated with the extension lead 16, and the proximal end of the extension lead 16 is removably mated to the control module 12 via a connector 22 associated with the control module 12.

In the illustrated embodiment, the control module 12 takes the form of an implantable pulse generator (IPG) that comprises an electronic subassembly 24 (shown in phantom), which includes control and pulse generation circuitry (not shown) for delivering electrical stimulation energy to the electrodes (described below) of the stimulation lead 14 in a controlled manner, and a power supply, e.g., a battery 26 (shown in phantom), so that once programmed and turned on by an external programming device (not shown), the control module 12 can operate independently of external hardware. Alternatively, the control module 12 can take the form of an implantable receiver-stimulator (not shown), in which case, the power source, e.g., a battery, for powering the implanted receiver, as well as control circuitry to command the receiver-stimulator, will be contained in an external controller inductively coupled to the receiver-stimulator via an electromagnetic link. Alternatively, the control module 12 can take the form of an external trial stimulator (ETS) (not shown), which has similar pulse generation circuitry as an IPG, but differs in that it is a non-implantable device that is used on a trial basis after the stimulation lead 14 has been implanted and prior to implantation of the IPG, to test the responsiveness of the stimulation that is to be provided.

The control module 12 comprises an outer housing 28 for housing the electronic and other components (described in further detail below), and the connector 22 to which the proximal end of the stimulation lead 14 mates in a manner that electrically couples the electrodes to the pulse generation circuitry contained within the outer housing 28. The outer housing 28 is composed of a biocompatible material, such as titanium, and forms a hermetically sealed compartment wherein the electronic subassembly 24 and battery 26 are protected from the body tissue and fluids. The connector 22 is disposed in a portion of the housing 28 that is, at least initially, not sealed. As will be described in further detail below, the connector 22 carries a plurality of contacts that come into electrical contact with the respective terminals (described in further detail below) of the stimulation lead 14 or extension lead 16 when the proximal end of the stimulation lead 14 or extension lead 16 is inserted into the connector 22. Electrical conductors (not shown), which extend from the connector 22 in electrical contact with the contacts, penetrate the housing 28 into the sealed chamber and connect to the electronic subassembly 24. Additional details discussing control modules, including the outer housing 28 and connector 22, are disclosed in U.S. patent application Ser. No. 11/327,880, entitled "Connector and Methods of Fabrication," which is expressly incorporated herein by reference.

As shown in FIG. 2, the stimulation lead 14 is implanted in the epidural space 30 of a patient in close proximity to the spinal cord 32. Because of the lack of space near the lead exit point 34 where the stimulation lead 14 exits the spinal column, the control module 12 is generally implanted in a surgically-made pocket either in the abdomen or above the buttocks. The control module 12 may, of course, also be implanted in other locations of the patient's body. Use of the extension lead 16 facilitates locating the control module 12 away from the lead exit point 34. In addition, in some cases, the extension lead may serve as a lead adapter if the proximal end of the stimulation lead 14 is not compatible with the connector of the control module 12 (e.g., different manufacturers use different connectors at the ends of their stimulation leads and are therefore not compatible with the connector heads of the control module of another manufacturer). The extension lead 16 may be made to adapt the stimulation lead 14 to connect the control module 12 to the stimulation lead 14, and hence, "adapt" the stimulation lead 14 to the control module 12.

Figure 3:
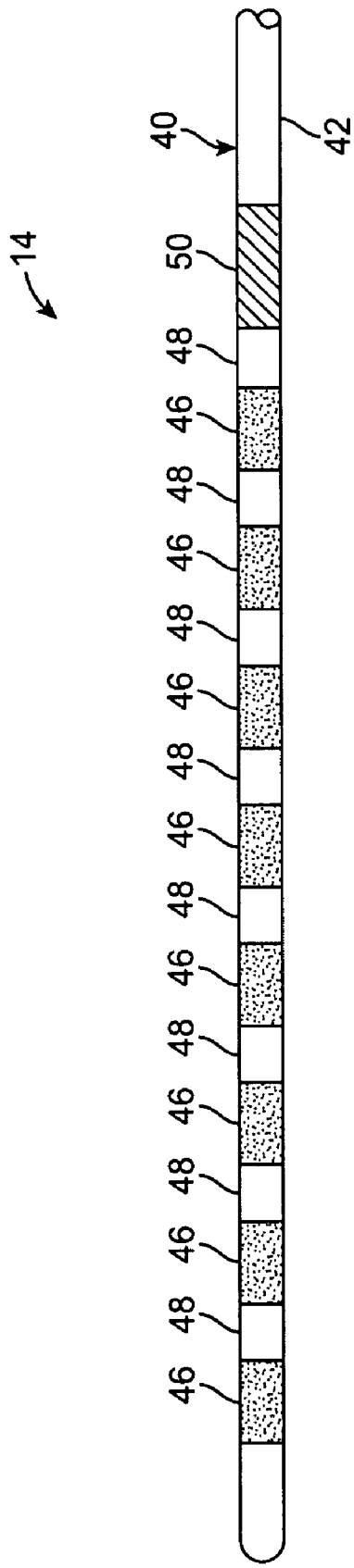
FIG. 3 is a profile view of a proximal end of a stimulation lead used in the tissue stimulation system of FIG. 1.
Figure 4:
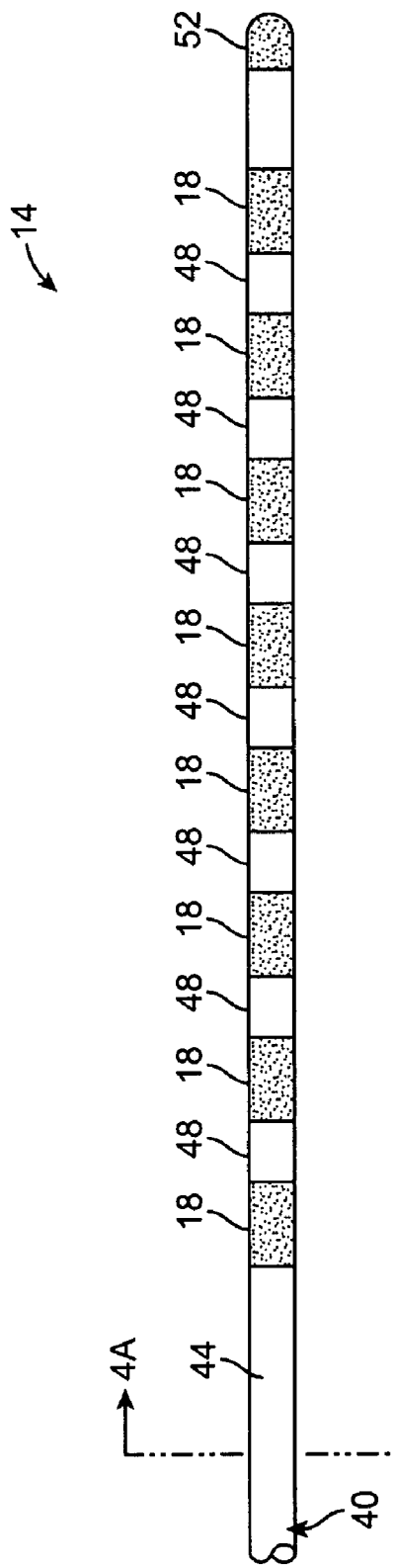
FIG. 4 is a profile view of a distal end of a stimulation lead used in the tissue stimulation system of FIG. 1.

Referring further to FIGS. 3 and 4, the stimulation lead 14 comprises an elongated lead body 40 having a proximal end 42 and a distal end 44. The lead body 40 may, e.g., have a diameter of between about 0.03 inches to 0.07 inches and a length within the range of 30 cm to 90 cm for spinal cord stimulation applications. The lead body 40 may be composed of a suitable electrically insulative material, such as, a polymer (e.g., polyurethane or silicone), and may be extruded from as a unibody construction.

The stimulation lead 14 further comprises a plurality of terminals 46 mounted to the proximal end 42 of the lead body 40 (FIG. 3), and the plurality of electrodes 18 mounted to the distal end 44 of the lead body 40 (FIG. 4). In the illustrated embodiment, the stimulation lead 14 is a percutaneous lead, and to this end, the electrodes 18 are arranged in-line along the lead body 40. In an alternative embodiment, the stimulation lead may take the form of a single paddle lead (not shown), in which case the electrodes 18 may be arranged in a two-dimensional pattern on one side of a paddle. Further details regarding the construction and method of manufacture of paddle leads are disclosed in U.S. patent application Ser. No. 11/319,291, entitled "Stimulator Leads and Methods for Lead Fabrication," the disclosure of which is expressly incorporated herein by reference.

Although the stimulation lead 14 is shown as having eight terminals 46 (FIG. 3) and eight corresponding electrodes 18 (FIG. 4), the number of terminals and electrodes may be any number suitable for the application in which the stimulation lead 14 is intended to be use (e.g., two, four, sixteen, etc.). Each of the terminals 46 and electrodes 18 takes the form of a cylindrical ring element composed of an electrically conductive, non-corrosive, material, such as, e.g., platinum, titanium, stainless steel, or alloys thereof.

The stimulation lead 14 further includes a plurality of electrically insulative spacers 48 located on the lead body 40 between the respective terminals 46 and electrodes 18. The spacers 48 may be composed of a suitable material, such as, a polymer (e.g., polyurethane or silicone). The stimulation lead 14 further includes an optional retention sleeve 50 located at the proximal end 42 of the lead body 40 just distal to the terminals 46. The retention sleeve 50 serves as a hard surface for a mechanical securing element, such as a set screw (not shown), used to secure the proximal end of the stimulation lead 14 within a connector (e.g., either carried by the extension lead or the control module). Alternatively, the retention sleeve 50 may be foregone, in which case, a set screw can be secured directly to one of the terminals 46. The stimulation lead 14 further comprises an optional radiopaque marker 52 located at the distal tip of the lead body 40.

Figure 4A:
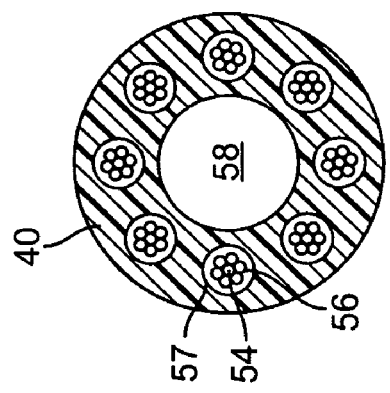
FIG. 4A is a cross-sectional view of the stimulation lead of FIG. 4, taken along the line 4A-4A.
Figure 5:
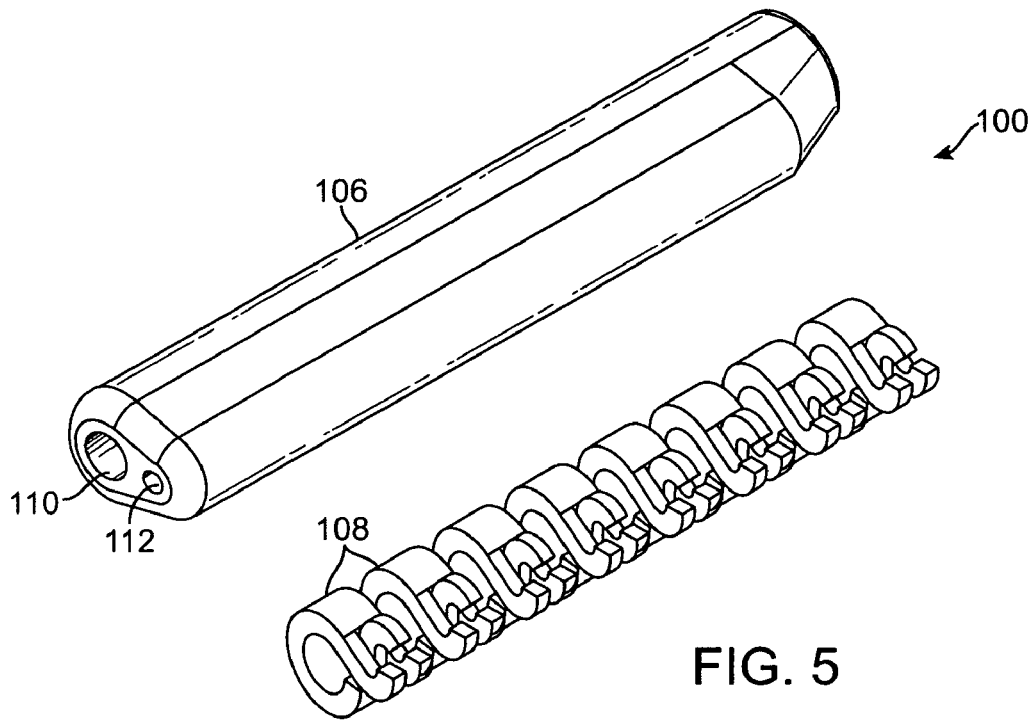
FIG. 5 is an exploded view of one embodiment of a connector that can be used in the tissue stimulation system of FIG. 1.

As shown in FIG. 4A, the stimulation lead 14 also includes a plurality of electrical conductors 54 (each comprising individual strands 56) extending through individual lumens 58 within the lead body 40 and connected between the respective terminals 46 and electrodes 18 using suitable means, such as welding, thereby electrically coupling the proximally-located terminals 46 with the distally-located electrodes 18. The stimulation lead 14 further includes a central lumen 58 that may be used to accept an insertion stylet (not shown) to facilitate lead implantation.

Further details describing the construction and method of manufacturing stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Referring back to FIG. 1, the extension lead 16 is similar to the stimulation lead 14 in that it comprises an elongated lead body 60 having a proximal end 62 and a distal end 64, and a plurality of terminals (not shown) mounted to the proximal end 62 of the lead body 60. The lead body 60 of the extension lead 16 may be similarly dimensioned and constructed as the lead body 40 of the stimulation lead 14. The extension lead 16 may also include retention sleeve (not shown) much like the retention sleeve 50 of the stimulation lead 14.

The extension lead 16 differs from the stimulation lead 14 in that, instead of electrodes, it comprises the previously mentioned connector 20 mounted to the distal end 64 of the lead body 60. The connector 20 is configured to accept the proximal end 42 of the stimulation lead 14. As will be described in further detail below, the connector 20 carries a plurality of contacts that come into electrical contact with the respective terminals 46 of the stimulation lead 14 when the proximal end 42 of the stimulation lead 14 is inserted into the connector 20. In a similar manner as the stimulation lead 14 (shown in FIG. 4), the extension lead 16 also includes a plurality of electrical conductors extending through individual lumens (both not shown) within the lead body 40 and connected between the respective terminals and contacts using suitable means, such as welding, thereby electrically coupling the proximally-located terminals with the distally-located contacts.

Referring now to FIGS. 5-9, one embodiment of a connector 100 that can be incorporated into the extension lead 16 and/or control module 12 (shown in FIGS. 1 and 2) will be described. As will be described in further detail below, the connector 100 can receive the proximal end of the electrical lead 102, which can be firmly engaged and locked within the connector 100 when a tool, and in particular a pin 104, is inserted into the connector 100. The electrical lead 102 may be, e.g., the stimulation lead 14 or the extension lead 16 (shown in FIGS. 1 and 2), depending on whether an extension lead is used in the lead assembly and whether the connector 100 is incorporated into an extension lead or in a control module. That is, if the connector 100 is to be located in an extension lead, the electrical lead that is mated within the connector 100 will be the stimulation lead. If the connector 100 is to be located in a control module, the electrical lead that is mated within the connector 100 will be the extension lead if used in the lead assembly and will be the stimulation lead if the extension lead is not used in the lead assembly. The pin 104 may be composed of a suitably rigid material, such as plastic or stainless steel.

Figure 6:
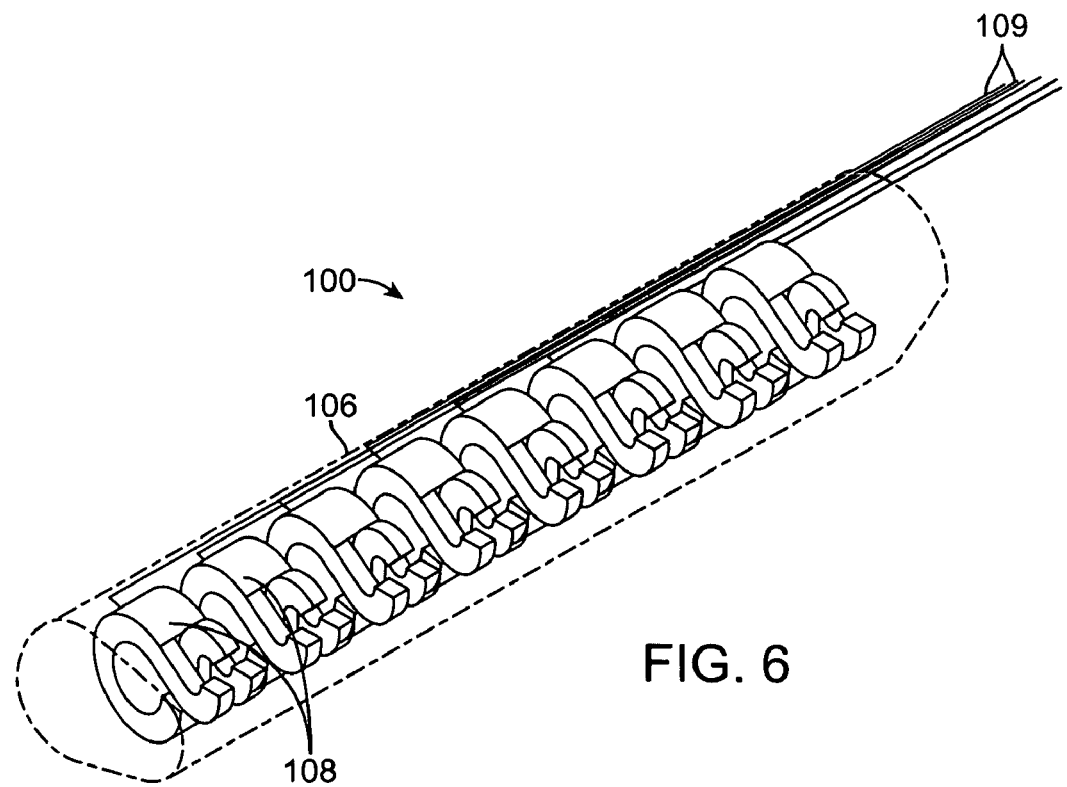
FIG. 6 is a perspective view of the connector of FIG. 5, particularly showing a receptacle of the connector in phantom.

The connector 100 generally comprises an electrically insulative receptacle 106 (shown in phantom in FIG. 6) and a plurality of electrical spring clip contacts 108 (in this case, eight) mounted within the receptacle 106. The receptacle 106 is composed of a suitable electrically insulative material, such as, silicone or polyurethane. In the illustrated embodiment, the receptacle 106 takes the form of a molded unibody structure in which the electrical contacts 108 can be disposed. As shown in FIG. 6, the connector 100 further comprises electrical conductors 109 respectively connected to the electrical contacts 108 using suitable techniques known in the art, such as welding. If the connector 100 is incorporated into an electrical lead, such as an extension lead, the electrical conductors 109 take the form of wires that are routed through the receptacle 106 (e.g., the electrical conductors 54 shown in FIG. 4A) and then through a lead body (not shown) that extends from the connector 100. If the connector 100 is incorporated into a control module, the electrical conductors 109 extend out from corresponding openings (not shown) made in the receptacle 109. Details discussing the manufacture of a unibody receptacle 106 are disclosed in U.S. patent application Ser. No. 11/327,880, which has previously been incorporated herein by reference. Alternatively, the receptacle 106 may be manufactured from several pieces that are then bonded together in a suitable manner to make an integrated body.

The receptacle 106 comprises a lead port 110 into which the proximal end of the electrical lead 102 can be introduced from a completely external position (FIG. 7) to an inserted position (FIG. 8), and a pin port 112 into which the pin 104 can be introduced from a completely external position (FIG. 7) to an inserted position (FIG. 9). As will be described in further detail below, before the pin 104 is inserted into the pin port 112, the electrical lead 102 can be repeatedly inserted into and removed from the receptacle 106 with very little force. However, once the pin 104 is inserted into the pin port 112 after the electrical lead 102 is inserted into the lead port 110, the connector 100 will firmly engage the electrical lead 102 until the pin 104 is removed from the pin port 112.

Figure 10:
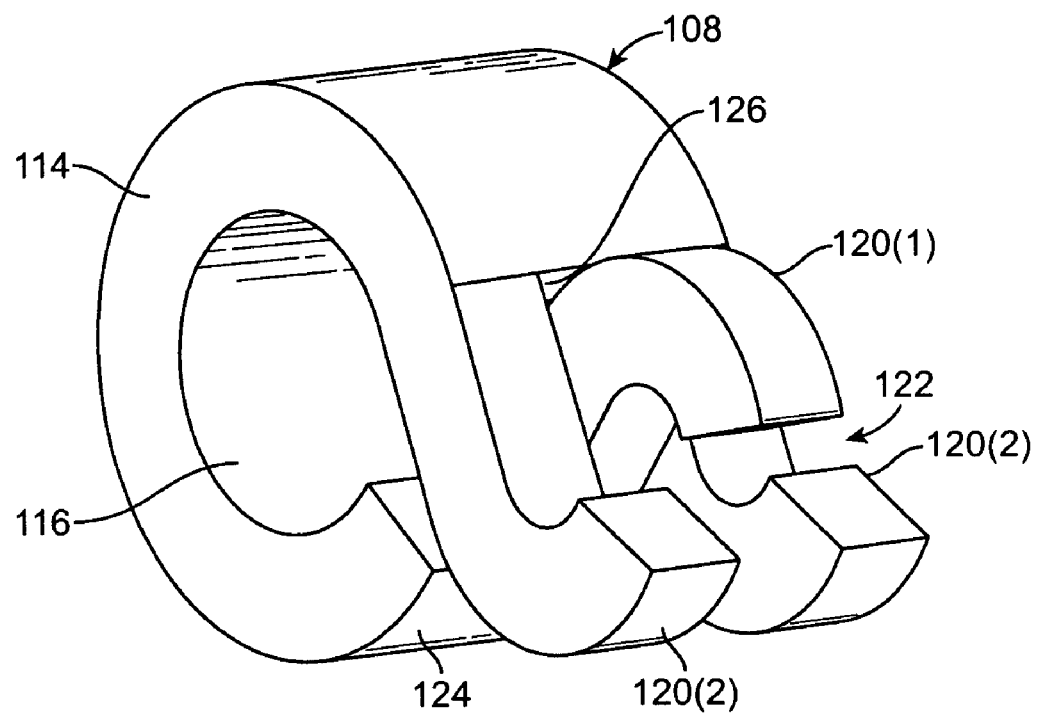
FIG. 10 is a perspective view of one electrical contact used in the connector of FIG. 5.
Figure 11:
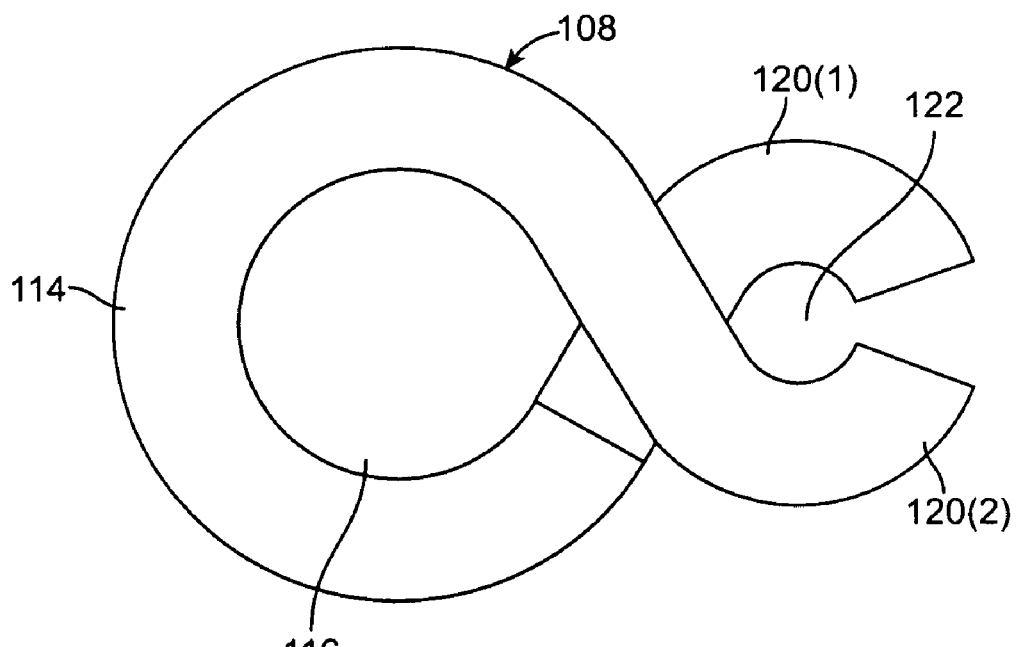
FIG. 11 is a side view of the electrical contact of FIG. 10.

Referring further to FIGS. 10 and 11, each of the electrical contacts 108 includes a collar 114 that forms a lead passage 116 for receiving a respective terminal 118 (shown in FIG. 7) carried by the proximal end of an electrical lead 102, and a plurality of lever arms 120 axially offset from each other (in this case, a single lever arm 120(1) interposed between, and opposing, a pair of lever arms 120(2)) that form a pin passage 122 for receiving the pin 104. Each electrical contact 108 is composed of a suitably resilient and electrically conductive material, such as, e.g., platinum, titanium, stainless steel, or alloys thereof. If stainless steel is used, an austenitic stainless steel, such as stainless steel 316, can be used.

In the illustrated embodiment, each electrical contact 108 is formed of a unibody design. In particular, the electrical contact 108 comprises a sheet of metal having an edge 124 from which the single lever arm 120(1) extends, and another opposing edge 126 from which the dual lever arms 120(2) extend. Preferably, the sheet of metal is made as a thin as possible to minimize the profile of the resulting connector, while maintaining its resiliency (i.e., springiness). Ultimately, the thickness of the sheet of metal will depend on the strength and elasticity of the material from which it is composed. By way of non-limiting example, the thickness of the sheet of metal may be in the range of 0.005 inches to 0.010 inches. The sheet of metal is wrapped around on itself to form the collar 114 with the lead passage 116 formed therein, as well as to cause the single lever arm 120(1) and the dual lever arms 120(2) to intersect a plane extending through the axis of the collar 114 from opposite directions. The free ends of the single lever arm 120(1) and dual lever arms 120(2) are curved back toward the plane to form the pin passage 122 through which the pin 104 is to be inserted.

The size and shapes of the passages 116, 122 will depend upon the cross-sectional size and shape of the proximal end of the electrical lead 102 and the pin 104, such that electrical contacts 108 can be interference fit with the terminals 118 on the electrical lead 102 when the electrical lead 102 is received within the lead port 110 and the lever arms 120 mechanically interact with the pin 104 when the pin 104 is received within the second port 112.

It is preferred that the pin passage 122 be minimized as much as possible to minimize the profile of the resulting connector 100. Because the diameter of the pin 104 can be made relatively small compared to the proximal end of the electrical lead 102, which must accommodate the terminals 118 and associated wires, the pin passage 122 through which the pin 104 extends will generally be much smaller than the lead passage 116 through which proximal end of the electrical lead 102 is inserted, thereby maximizing the usage of space within the receptacle 106 for the electrical lead 102 itself.

In the embodiment illustrated in FIGS. 10 and 11, the sheet of metal is wrapped around on itself in a manner that causes the collar 114, and thus the lead passage 116, to have a circular cross-section. The lever arms 120 are curved back toward the plane in a manner that causes the pin passage 122 to assume a circular cross-section. In this case, the connector 100 is specifically adapted to be used with an electrical lead 102 and pin 104 that have circular cross-sections.

Figure 12:
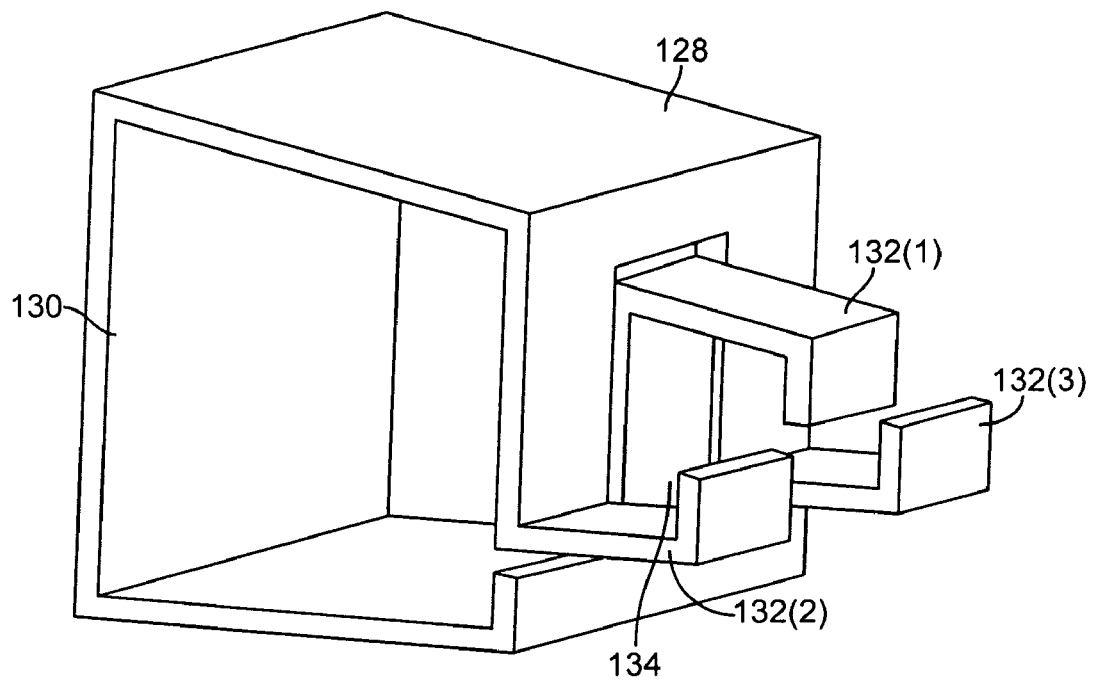
FIG. 12 is a perspective view of another electrical contact that can be used in the connector of FIG. 5.

Alternatively, as shown in FIG. 12, the sheet of metal can be wrapped around on itself in a manner that causes a collar 128, and thus a first passage 130 extending through the collar, to have a rectangular cross-section. Lever arms 132 (a single lever arm 132(1) interposed between, and opposing, dual lever arms 132(2)) are curved back toward the plane in a manner that causes a second passage 134 to assume a generally rectangular cross-section. In this case, the connector 100 would specifically be adapted to be used with an electrical lead 102 and pin 104 that have rectangular cross-sections. The lead and pin passages respectively formed by the collar and lever arms can have other cross-sectional shapes, such as, e.g., triangular, octagonal, oval, elliptical, etc.

Figure 13:
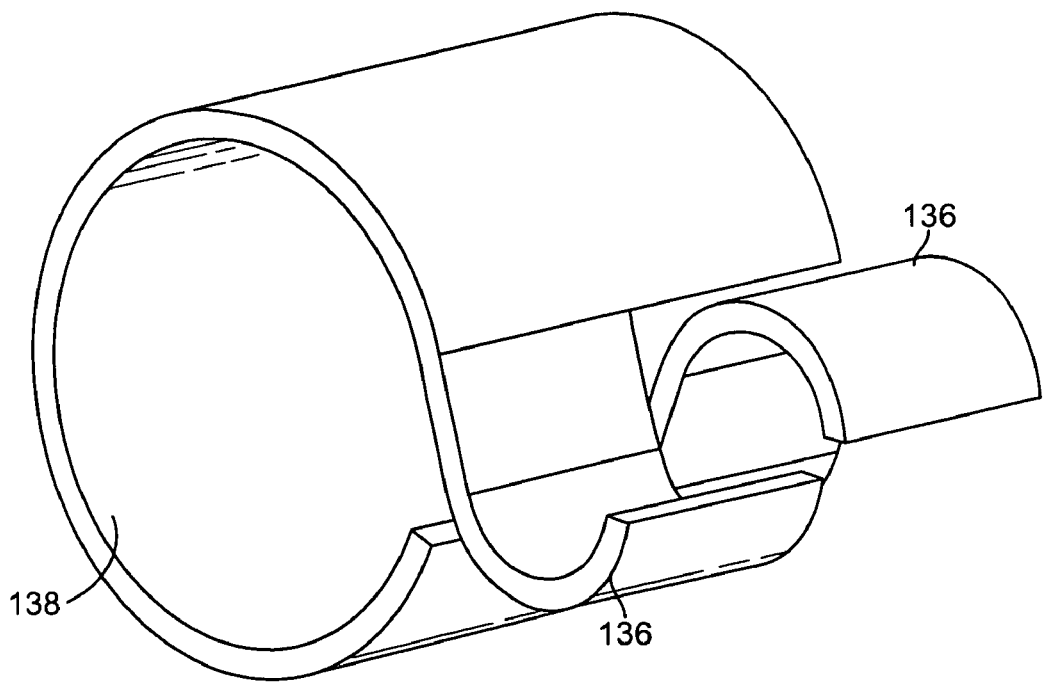
FIG. 13 is a perspective view of still another electrical contact that can be used in the connector of FIG. 5.

It should be appreciated that although the electrical contact 108 illustrated in FIGS. 10 and 11 comprises three lever arms, an electrical contact can comprise any number of lever arms, such as, e.g., two, four, five, etc. For example, as illustrated in FIG. 13, two axially offset lever arms 136 are curved back toward a plane extending through the axis of the collar to form a second passage 138 through which the pin 104 is to be inserted.

Figure 14:
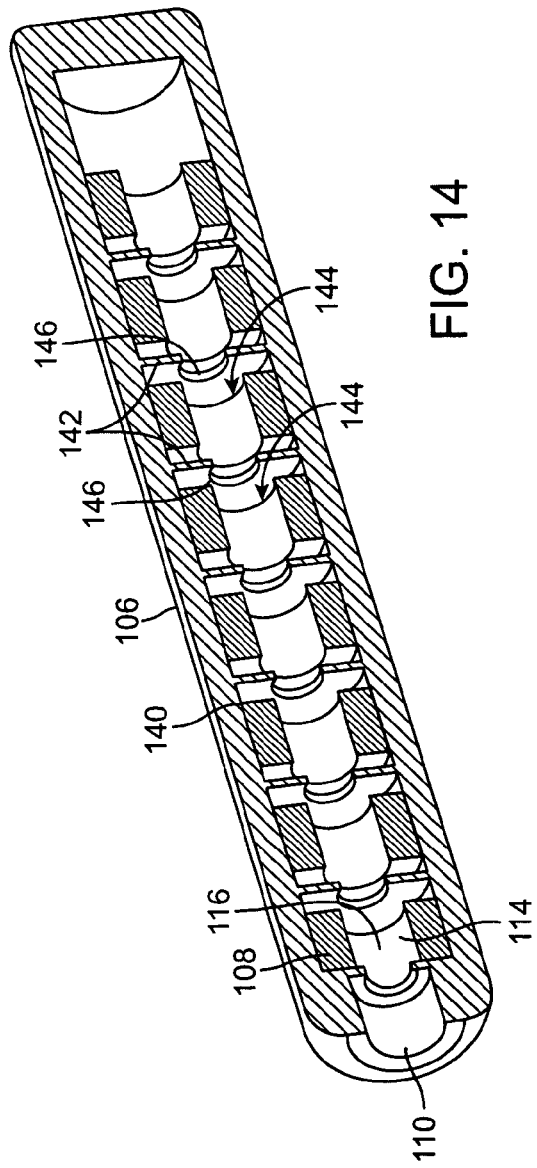
FIG. 14 is a cross-sectional perspective view of the connector of FIG. 5, particularly taken along a lead port of the connector.
Figure 16:
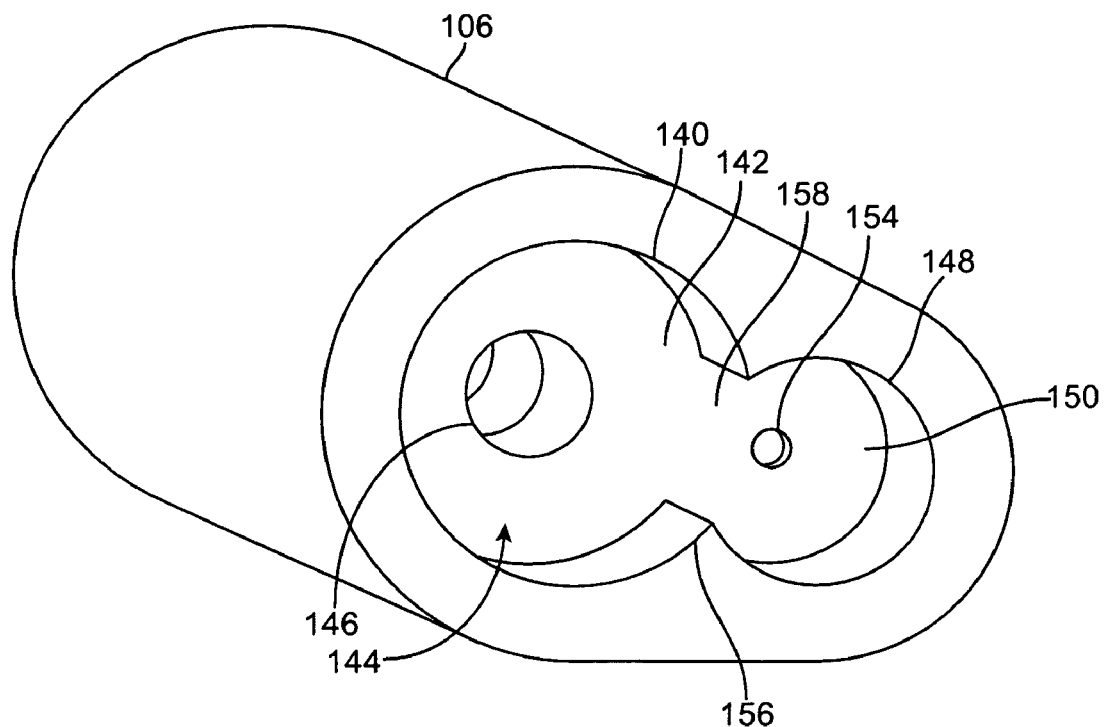
FIG. 16 is a cross-sectional perspective view of a receptacle of the connector of FIG. 5, particularly taken transversely to the axis of the connector.

Referring further to FIGS. 14 and 16, the receptacle 106 comprises a first elongated cavity 140 along which the collars 114 of the electrical contacts 108 are disposed and spaced apart in a single row, such that the inner surfaces of the collars 114 are respectively placed into contact with the electrical terminals 118 (shown in FIG. 7) when the proximal end of the electrical lead 102 (shown in FIG. 7) is introduced into the lead port 110 and fully received within the elongated cavity 140. In the illustrated embodiment, the electrical contacts 108 are spaced apart along the cavity 140 at substantially uniform intervals, although in alternative embodiments, the electrical contacts 108 can be spaced apart at non-uniform intervals. Ultimately, the spacing of the electrical contacts 108 will be selected to match the spacing of the electrical terminals 118 carried by the proximal end of the electrical lead 102.

In the illustrated embodiment, the electrical contacts 108 are electrically isolated from each other within the elongated cavity 140. To this end, each electrical contact 108, with the exception of the inner surface of the electrical contact 108 where electrical contact with the respective terminal 118 (shown in FIG. 7) of the electrical lead 102 (shown in FIG. 7) is required is coated within an electrically insulative material, such as Teflon®, or anodized to increase the natural oxide layer on the surface of the electrical contact 108. During coating or anodization of the electrical contact 108, a mandrel can be inserted through lead passage 116 of electric contact 108, so that the inner surface of the contact 108 surrounding the lead passage 116 (i.e., the surface intended to contact the respective terminal 118 of the electrical lead 102) is not coated or anodized, and thus remains electrically conductive. The mandrel can be coated with a material that affords a good seal between the inner surface of the contacts 108 and the mandrel, thus preventing any insulative coating from adhering to the inner surface of the contacts 108. The mandrel can also be used as part of any overmolding process used to dispose the receptacle 106 over the contacts 108.

To further maximize isolation between the electrical contacts 108 within the first cavity 140, the receptacle 106 further comprises a plurality of seals 142 that respectively form annular pockets 144 therebetween in which the collars 114 of the electrical contacts 108 are disposed. The seals 142 generally electrically isolate electrical circuitry located in each connector pocket 144. For example, the seals 142 may electrically isolate each connection between an electrical contact 108 and a respective electrical terminal 118 of the lead 102 (shown in FIG. 7). In the illustrated embodiment, each seal 142 takes the form of an O-ring that extends from the inner surface of the receptacle 106 into the elongated cavity 140, such that when the proximal end of the electrical lead 102 is inserted into the cavity 140 and through center openings 146 in the seals 142, the seals 142 will conform to, and thereby seal, against the outer surface of the electrical lead 102. As a result, even if an electrolytic fluid enters the cavity 140 of the receptacle 106, the seals 142 will prevent or, at least minimize, the leakage of electrical current between the electrical contacts 108.

Figure 15:
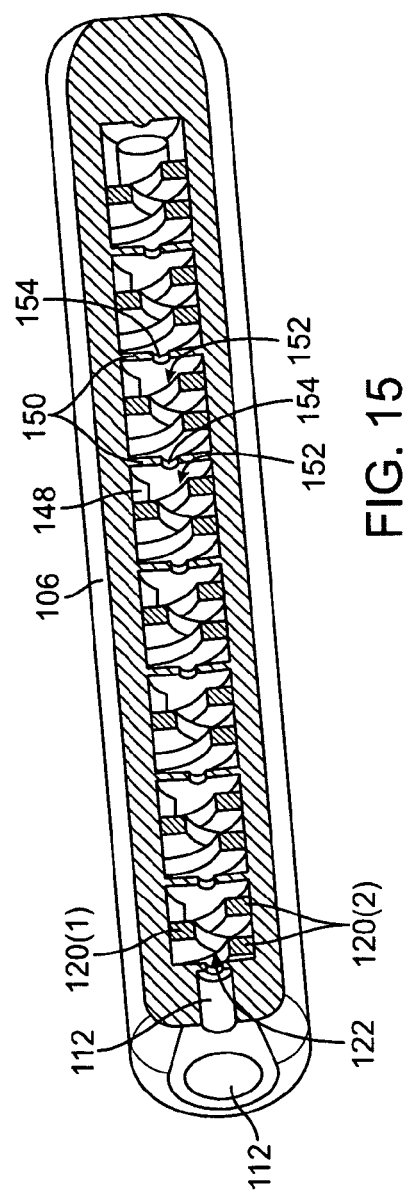
FIG. 15 is a cross-sectional perspective view of the connector of FIG. 5, particularly taken along a pin port of the connector.

Referring further to FIG. 15, the receptacle 106 comprises a second elongated cavity 148 along which the lever arms 120 of the electrical contacts 108 are disposed and spaced apart in a single row, such that the inner surfaces of the lever arms 120 are respectively placed into contact with the pin 104 is introduced into the pin port 112 and fully received within the elongated cavity 148.

To further maximize isolation between the electrical contacts 108 within the second cavity 148, the receptacle 106 further comprises a plurality of seals 150 that respectively form annular pockets 152 therebetween in which the lever arms 120 of the electrical contacts 108 are disposed. In the illustrated embodiment, each seal 150 takes the form of an O-ring that extends from the inner surface of the receptacle 106 into the elongated cavity 148, such that when the pin 104 is inserted into the cavity 148 and through center openings 154 in the seals 150, the seals 150 will conform to, and thereby seal, against the outer surface of the pin 104. As a result, even if an electrolytic fluid enters the cavity 148 of the receptacle 106, the seals 150 will prevent or, at least minimize, the leakage of electrical current between the lever arms 120.

As best shown in FIG. 16, the receptacle 106 further comprises a septum 156 located between the respective elongated cavities 140, 148, and an opening 158 formed through the septum 156 between each corresponding pair of annular pockets 144, 152, thereby providing access from the annular pockets 144 to the annular pockets 152, so that the lever arms 120 of the respective electrical contacts 108 can extend from the collars 114 located in the first elongated cavity 140 into the second elongated cavity 148 unimpeded. Preferably, all of the openings 158 are aligned in a manner that likewise aligns the lever arms 120, such that the pin 104 can seamlessly pass though the pin passages 122 formed by the lever arms 120.

As briefly discussed above, the proximal end of the electrical lead 102 may effortlessly be inserted into and withdrawn from the lead port 110 when the pin 104 has not been inserted into the pin port 112, and may be firmly engaged by the receptacle 106 after the pin 104 has been inserted into the pin port 112. This function is effected by the direct interaction between the pin 104 and the lever arms 120 of the respective electrical contacts 108; that is, advancement of the pin 104 through the pin passages 122 of the electrical contacts 108 causes the collars 114 of the electrical contacts 108 to constrict firmly around the respective terminals 118 of the electrical lead 102, whereas removal of the pin 104 from the pin passages 122 of the electrical contacts 108 causes the collars 114 of the electrical contacts 108 to release the respective terminals 118 of the electrical lead 102.

Figure 17:
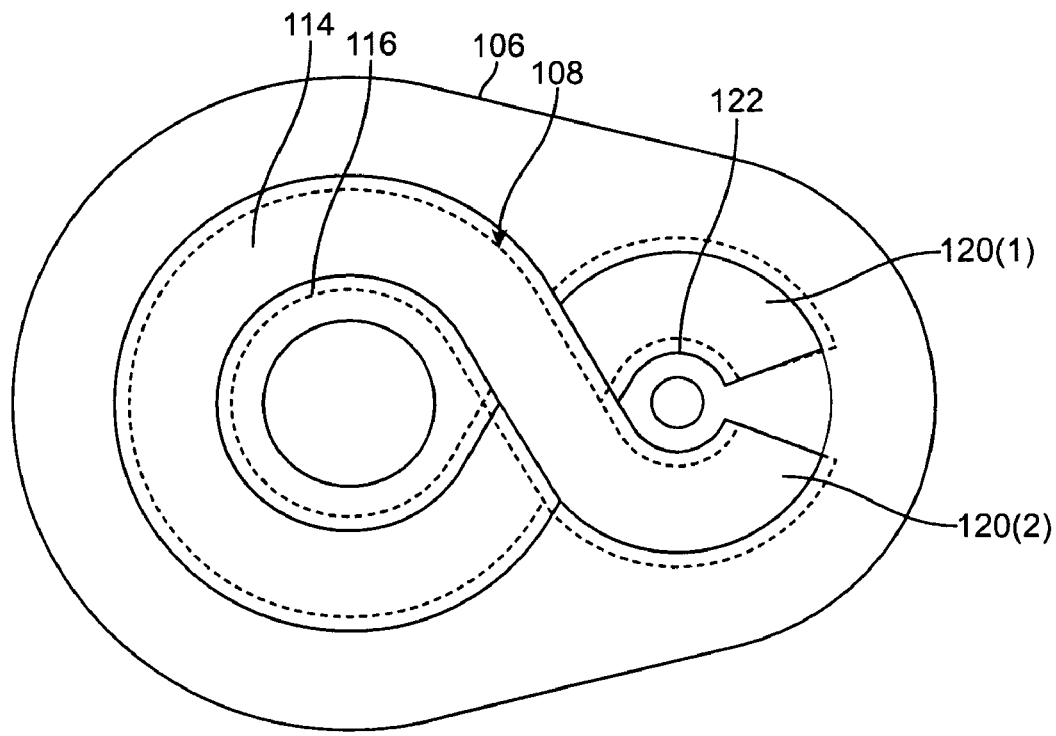
FIG. 17 is a cross-sectional view of the connector of FIG. 5, particularly taken transversely to the axis of the connector.

In particular, before the pin 104 is introduced into the lead port 110, each electrical contact 108 has a relaxed state during which the spring force of the electrical contact 108 naturally urges the respective collar 114 into an expanded state (shown in FIG. 17), so that the lead passage 116 has a diameter slightly greater than the diameter of the electrical lead 102 (shown in FIG. 7), and during which the single lever arm 120(1) and dual lever arms 120(2) (only one shown in FIG. 17) are displaced toward each other, so that the pin passage 122 of each electrical contact 108 has a diameter slightly smaller than the diameter of the pin 104. As a result, the proximal end of the electrical lead 102, when inserted into the lead port 110, easily passes through the lead passages 116 of the respective electrical contacts 108 with a minimal amount of insertion force. When the pin 104 is inserted into the pin port 112, the pin 104 displaces the single lever arm 120(1) and dual lever arms 120(2) (only one shown in FIG. 17) of each electrical contact 108 away from each other. As a result, the collar 114 of each electrical contact 108 is placed into a collapsed state (shown in phantom in FIG. 17), thereby firmly engaging the respective terminals 118 of the electrical lead 102.

In an alternative embodiment, rather than using a pin port 112, the lever arms 120 of the respective electrical contacts 108 are exposed outside of the receptacle 106, so that the pin 104 can be inserted through the pin passages 122 of the electrical contacts 108 without initially passing through a pin port 112. In this case, a seal cover, such as the seal cover used with the connector described below, can be mounted to the receptacle 106 over the exposed lever arms 120 after the pin 104 has been inserted through the pin passages 122.

Referring now to FIGS. 18-21, another embodiment of a connector 200 that can be incorporated into the extension lead 16 and/or control module 12 (shown in FIGS. 1 and 2) will be described. Like the connector 100, the connector 200 can receive the proximal end of the electrical lead 102 (shown in FIG. 7), which can be firmly engaged and locked within the connector 200. As with the connector 100, the electrical lead 102 may be, e.g., the stimulation lead 14 or the extension lead 16 (shown in FIGS. 1 and 2). In contrast to the connector 100, a tool 204 (shown in FIG. 30) is inserted into the connector 200 and expanded to allow the electrical lead 102 to be received within the connector 200, and then contracted and removed to firmly engage and lock the electrical lead 102 within the connector 200. Alternatively, the pin 104 (shown in FIG. 7) can be inserted into the connector 200 to allow the electrical lead 102 to be received within the connector 200, and then removed to firmly engage and lock the electrical lead 102 within the connector 200.

Figure 30:
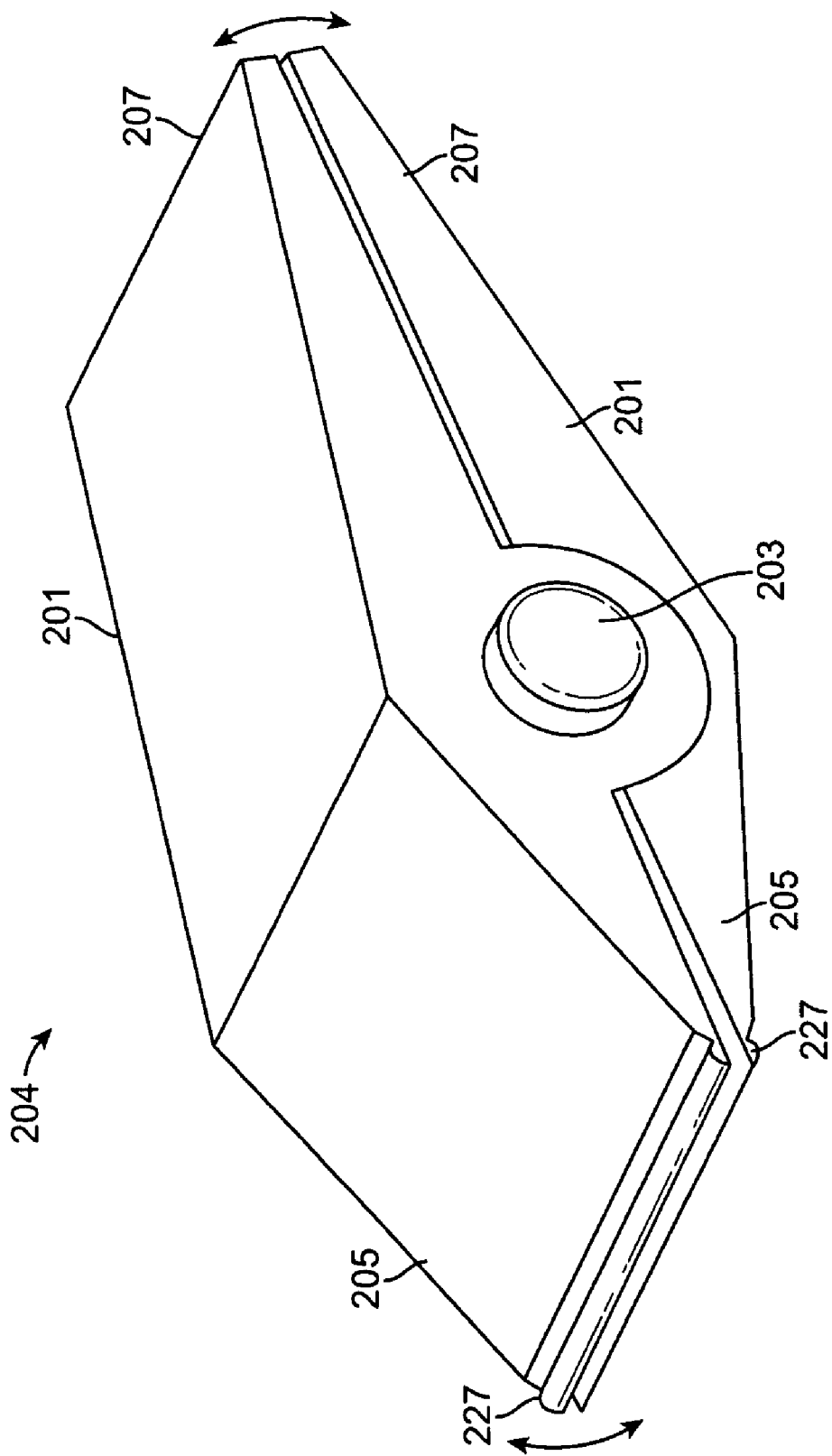
FIG. 30 is a perspective view of a tool that can be used with the connector of FIG. 18.

As shown in FIG. 30, the tool 204 comprises a pair of arms 201 and a pin 203 that hinges the arms 201 together. The arms 201 have distal ends 205 that can be alternately displaced toward each other to place the tool 204 in a closed state and away from each other to place the tool 204 in an open state (as shown by the arrows). The pin 203 is spring-loaded, such that the tool 204 is urged into the closed position. The lever arms 201 have proximal ends 207 that can be displaced toward each other, thereby causing the distal ends 205 of the lever arms 201 to be displaced away from each other to place the tool 204 in the open state. The tool 204 further comprises a mating element 227 disposed on the outer surfaces of each of the distal ends 205, which interact with the connector 200 to allow the electrical lead 102 to be easily inserted into the connector 200 with little insertion force, as will be described in further detail below. Preferably, the tool 204 is designed to provide a mechanical force advantage, while limiting the opening of the distal ends 205 of the arms 201, thereby preventing deformation of the connector 200. The length of the arms 201, the position of the pin 203 relative to the arms 201, and the distance of mating elements 225 to the pin 203 all determine the amount that the mating elements 227 are displaced, as well as the force advantage of the tool 200.

Referring back to FIGS. 18-21, the connector 200 generally comprises an electrically insulative receptacle 206 (shown in phantom in FIG. 20), and a plurality of electrical spring clip contacts 208 (in this case, eight) mounted within the receptacle 206. The receptacle 206 is composed of a suitable electrically insulative material, such as, silicone or polyurethane. Similar to the previously described receptacle 106, the receptacle 206 may take the form of a molded unibody structure, or alternatively, several pieces that are then bonded together in a suitable manner to make an integrated body. In the same manner as the connector 100, the connector 200 further comprises electrical conductors 209 (shown in FIG. 20) respectively connected to the electrical contacts 208 using suitable techniques known in the art, such as welding. The connector 200 further includes an electrically insulative seal cover 211 that can be mounted onto the receptacle 206 over the exposed portions of the electrical contacts 208.

Figure 7:
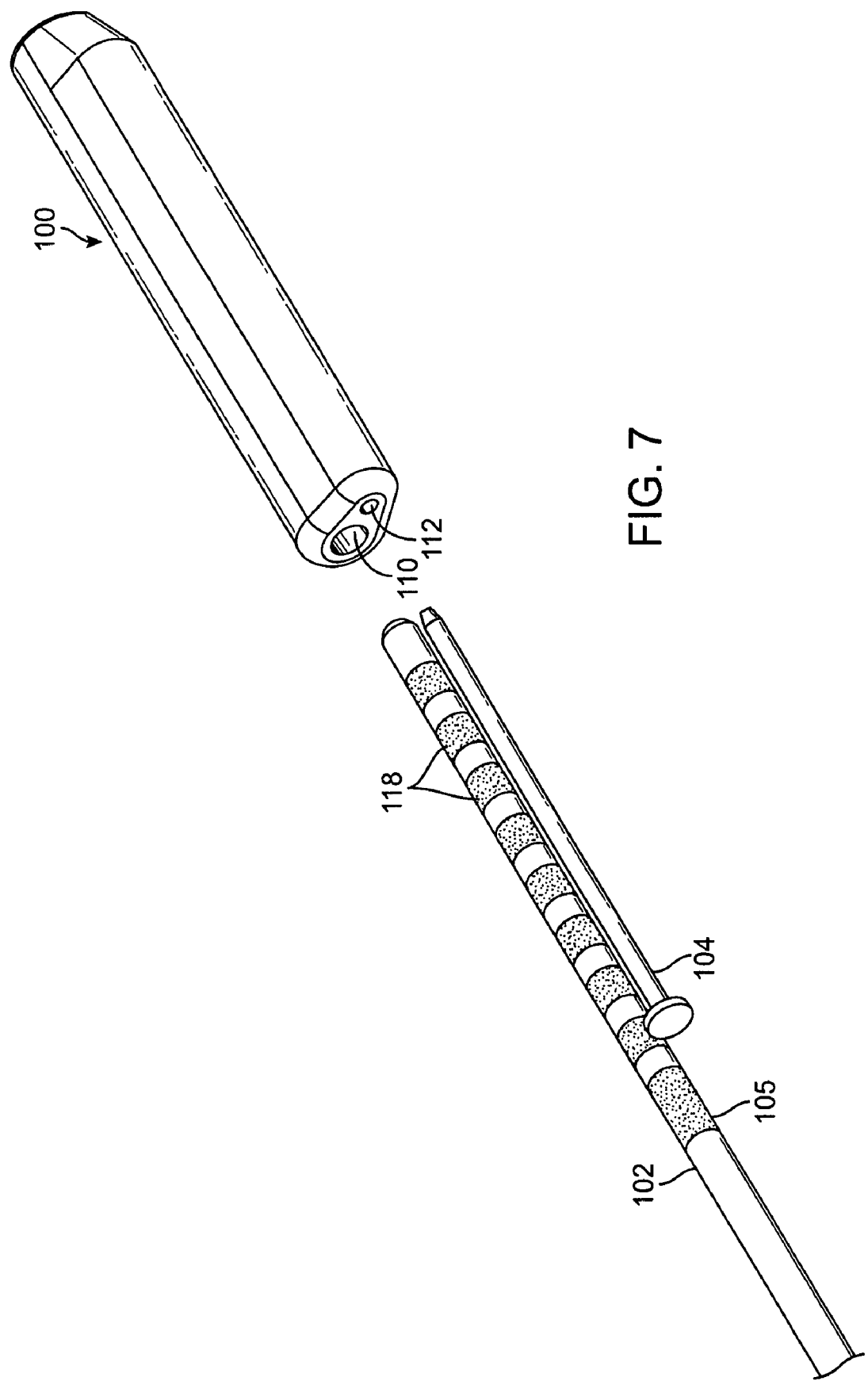
FIG. 7 is a perspective view of the connector of FIG. 5, particularly showing a stimulation lead and pin external to the connector.

The receptacle 206 comprises an enlarged portion 213, a lead port 210 formed within expanded portion 213 into which the proximal end of the electrical lead 102 can be introduced, and a securement opening 215 through which a tool (e.g., a torque wrench), such as a screwdriver, may tighten and loosen a set screw (not shown) that can be used to more firmly secure the electrical lead 102 (e.g., by frictionally engaging a retention sleeve 105 shown in FIG. 7) within the receptacle 206.

As best shown in FIG. 19, the connector 200 further comprises a connector block 217 mounted within the enlarged portion 213 of the receptacle 206. The connector block 217 serves a rigid platform for supporting the forces applied to the set screw. To this end, the connector block 217 includes a threaded bore 219 corresponding to the securement opening 215 in the receptacle 206, and an unthreaded bore 221 corresponding to the lead port 210 of the receptacle 206. The set screw is disposed in the threaded bore 219, and the unthreaded bore 221 receives the proximal end of the electrical lead 102. As shown, the unthreaded bore 221 is offset from the center of the connector block 217, thereby allowing enough thickness in the wall to support the thread depth of the setscrew.

The connector block 217 can be composed of any suitable conductor or non-conductive material, such as, e.g., non-conductive polymers, polyetheretherketone (PEEK), ceramics, etc., metal, alloys, conductive polymers, conductive carbon, etc. As will be described in further detail below, because it is expected that the retention force between the electrical contacts 208 and the terminals 118 will firmly secure the electrical lead 102 within the receptacle 206 (with the retention force increasing with the number of electrical contacts 208), the use of the connector block 217, along with the enlarged portion 213 of the receptacle 206, may be foregone in most cases, thereby minimizing the profile of the connector 200.

Figure 22:
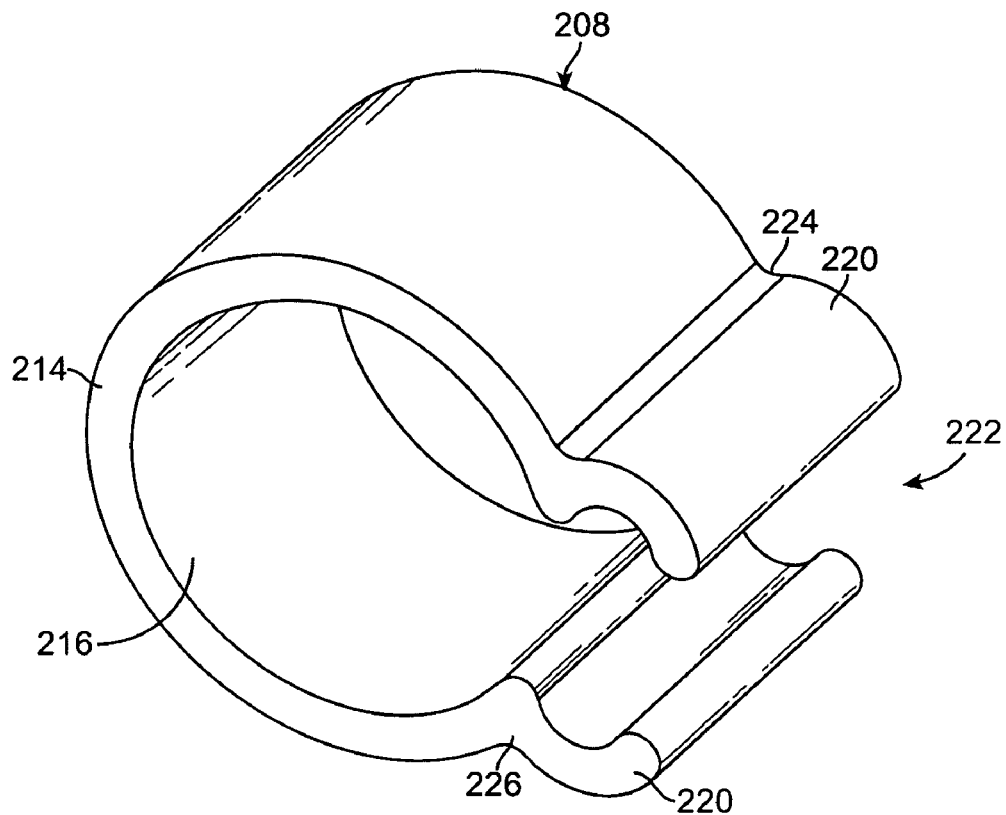
FIG. 22 is a perspective view of one electrical contact used in the connector of FIG. 18.
Figure 23:
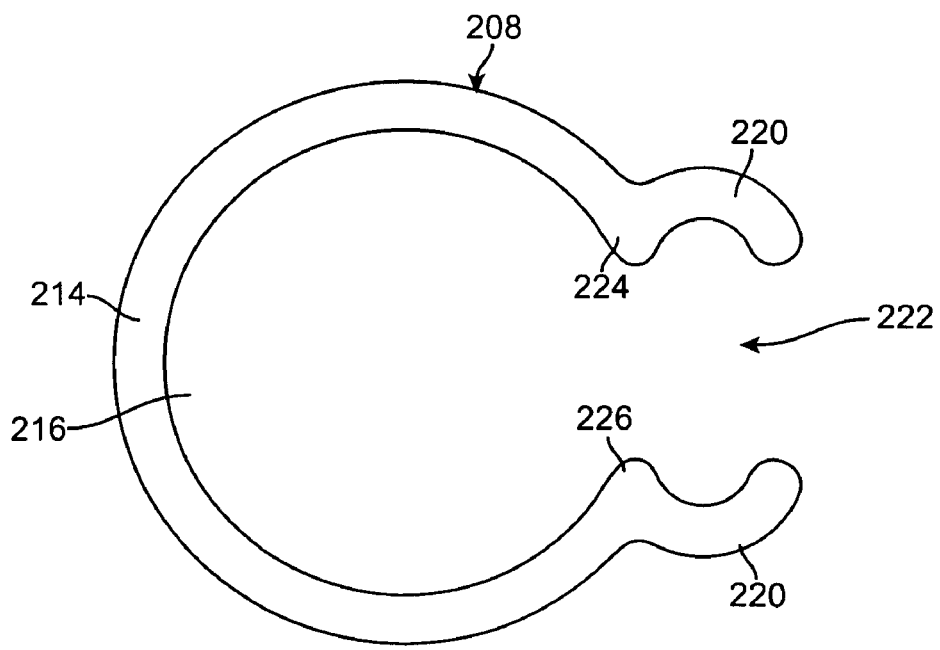
FIG. 23 is a side view of the electrical contact of FIG. 22.

Referring further to FIGS. 22 and 23, each of the electrical contacts 208 includes a collar 214 that forms a lead passage 216 for receiving a respective terminal 118 (shown in FIG. 7) carried by the proximal end of an electrical lead 102, and a pair of lever arms 220 that form a tool passage 222 for receiving the mating elements 227 of the tool 204. Each electrical contact 208 is composed of a suitably resilient and electrically conductive material, such as, e.g., platinum, titanium, stainless steel, or alloys thereof. If stainless steel is used, an austenitic stainless steel, such as stainless steel 316, can be used.

Ultimately, the material from which each electrical contact 208 is composed should have the necessary spring properties that allow the collar 214 of the electrical contact 208 to grip the respective terminal 118 of the electrical lead 106 with high retention force. To increase the retention force, the inner surface of the collar 214 and the outer surface of the terminal 118 may optionally include corresponding mating features, thereby allowing the electrical contact 208 and respective terminal 118 to lock together when the collar 214 is released onto the terminal 118, as will be described in further detail below. For example, as shown in FIG. 24, the collar 214 may include an annular ridge 223 that extends around the entire circumference of its inner surface, and the terminal 118 includes a corresponding annular recess 225 that extends around the entire circumference of its outer surface. Alternatively, the annular ridge 223 and annular recess 225 may not extend entirely around the circumference of the respective collar 214 and terminal 118. These corresponding mating features can be incorporated into the proximal-most contacts 208/terminals 118, several of the contacts 208/terminals 118, or all of the contacts 208/terminals 118 to facilitate alignment and increased retention of the electrical lead 106 within the connector 200.

In the illustrated embodiment, each electrical contact 208 is formed of a unibody design. In particular, the electrical contact 208 comprises a sheet of metal having an edge 224 from which one of the lever arms 220 extends, and another opposing edge 226 from which the other lever arm 220 extends. Preferably, the sheet of metal is made as a thin as possible to minimize the profile of the resulting connector, while maintaining its resiliency (i.e., springiness). Ultimately, the thickness of the sheet of metal will depend on the strength and elasticity of the material from which it is composed. By way of non-limiting example, the thickness of the sheet of metal may be in the range of 0.003"-0.010", and preferably in the range of 0.004"-0.006". The sheet of metal is wrapped around on itself to form the collar 214 with the lead passage 216 formed therein, as well as to cause the lever arms 220 to oppose each other. The lever arms 220 are curved toward each other to form the tool passage 222 in which the mating elements 227 of the tool 204, which take the form of ridges or protuberances, will be located, as will be described in further detail below. Alternatively, the lever arms 220 may be curved away from each other to form curved ridges or protuberances (not shown) that face each other in which opposing depressions (not shown) of the tool 204 can be located.

The size and shape of the passages 216, 222 will depend upon the cross-sectional size and shape of the proximal end of the electrical lead 102 and the distal ends 205 of the tool 204, such that electrical contacts 208 can be interference fit with the terminals 118 on the electrical lead 102 when the electrical lead 102 is received within the lead port 210 and the mating elements 227 of the tool 204 mechanically interact with the lever arms 220 of the electrical contact 208.

It is preferred that the tool passage 222 be minimized as much as possible to minimize the profile of the resulting connector 200. Because the profile of the mating elements 227 of the tool 204 can be made relatively small compared to the proximal end of the electrical lead 102, which must accommodate the terminals 118 and associated wires, the tool passage 222 will generally be much smaller than the lead passage 216 though which proximal end of the electrical lead 102 is inserted, thereby maximizing the usage of space within the receptacle 206 for the electrical lead 102 itself.

Referring further to FIG. 25, the receptacle 206 comprises an elongated cavity 240 along which the collars 214 of the electrical contacts 208 are disposed and spaced apart in a single row, such that the inner surfaces of the collars 214 are respectively placed into contact with the electrical terminals 118 when the proximal end of the electrical lead 102 is introduced into the lead port 210 and fully received within the elongated cavity 240. In the illustrated embodiment, the electrical contacts 208 are spaced apart along the cavity 240 at substantially uniform intervals, although in alternative embodiments, the electrical contacts 208 can be spaced apart at non-uniform intervals. Ultimately, the spacing of the electrical contacts 208 will be selected to match the spacing of the electrical terminals 118 carried by the proximal end of the electrical lead 102.

In the illustrated embodiment, the electrical contacts 208 are electrically isolated from each other within the elongated cavity 240. To this end, each electrical contact 208, with the exception of the inner surface of the electrical contact 208 where electrical contact with the respective terminal 118 of the electrical lead 102 is required is coated within an electrically insulative material, such as Teflon®, or anodized to increase the natural oxide layer on the surface of the electrical contact 208. During coating or anodization of the electrical contact 208, a mandrel can be inserted through lead passage 216 of electric contact 208, so that the inner surface of the contact 208 surrounding the lead passage 216 (i.e., the surface intended to contact the respective terminal 118 of the electrical lead 102) is not coated or anodized, and thus remains electrically conductive. The mandrel can be coated with a material that affords a good seal between the inner surface of the contacts 208 and the mandrel, thus preventing any insulative coating from adhering to the inner surface of the contacts 208. The mandrel can also be used as part of any overmolding process used to dispose the receptacle 206 over the contacts 208.

To further maximize isolation between the electrical contacts 208, the receptacle 206 further comprises a plurality of seals 242 that respectively form annular pockets 244 therebetween in which the collars 214 of the electrical contacts 208 are disposed. The seals 242 generally electrically isolate electrical circuitry located in each connector pocket 244. For example, the seals 242 may electrically isolate each connection between an electrical contact 208 and a respective electrical terminal 118 of the lead 102. In the illustrated embodiment, each seal 242 takes the form of an O-ring that extends from the inner surface of the receptacle 206 into the elongated cavity 240, such that when the proximal end of the electrical lead 102 is inserted into the cavity 240 and through center openings 246 in the seals 242, the seals 242 will conform to, and thereby seal, against the outer surface of the electrical lead 102. As a result, even if an electrolytic fluid enters the cavity 240 of the receptacle 206, the seals 242 will prevent or, at least minimize, the leakage of electrical current between the electrical contacts 208.

As best shown in FIG. 21, the receptacle 206 further comprises openings 258 leading to the respective annular pockets 244, thereby allowing the lever arms 220 to exit out of the annular pockets 244 for manipulation by the tool 204. Preferably, all of the openings 258 are aligned in a manner that likewise aligns the lever arms 220, such that the mating elements 227 of the tool 204 can be easily located through the tool passages 222 formed by the lever arms 220. In the illustrated embodiment, the openings 258 may be slightly smaller than the cross-sections of the lever arms 220, so that the annular pockets 244 in the elongated cavity 240, and thus, the terminals 118 on the electrical lead 102, are electrically isolated from fluids external to the receptacle 206. Alternatively, the openings 258 may be large enough, so that the annular pockets 244 are exposed to the exterior of the receptacle 206. As will be described in further detail below, the seal cover 211 will electrically isolate the terminals 118 of the electrical lead 102 residing in the respective annular pockets 244 from fluid even if the openings 258 expose the terminals 118 to the exterior of the receptacle 206.

Figure 26:
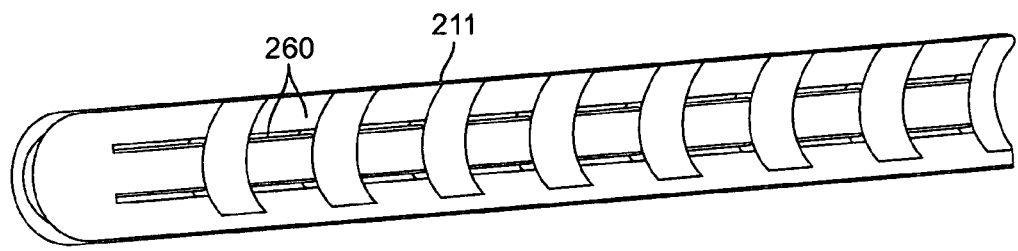
FIG. 26 is a cut-away perspective view of a seal cover used in the connector of FIG. 18, particularly taken along the axis of the seal cover.
Figure 27:
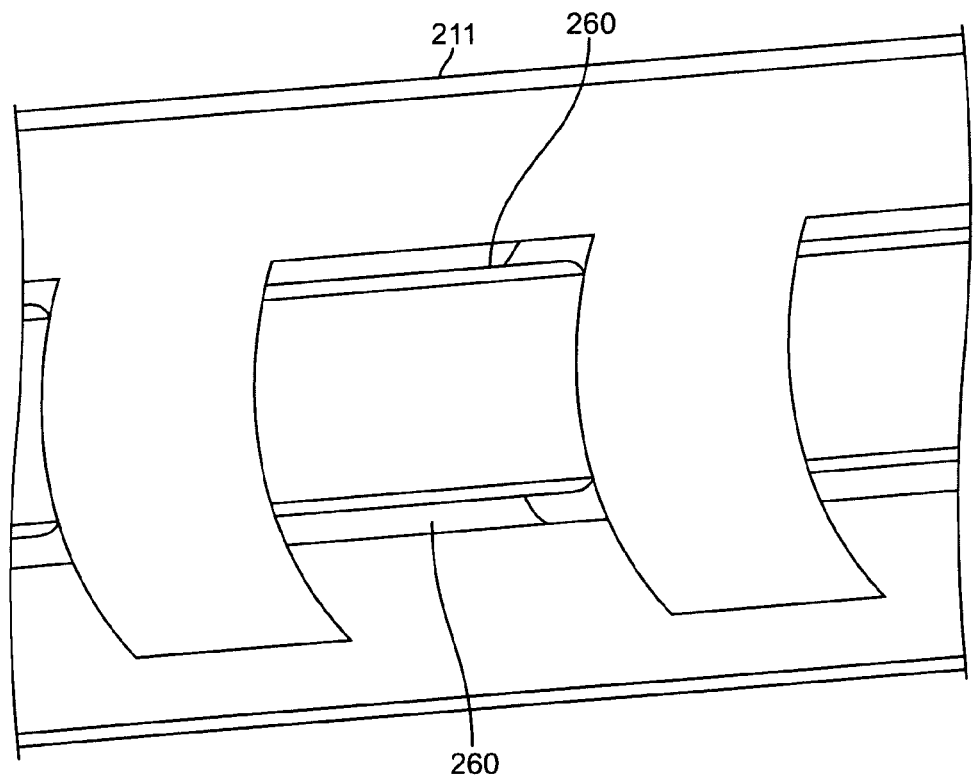
FIG. 27 is a cross-sectional perspective close-up view of the seal cover of FIG. 26.
Figure 28:
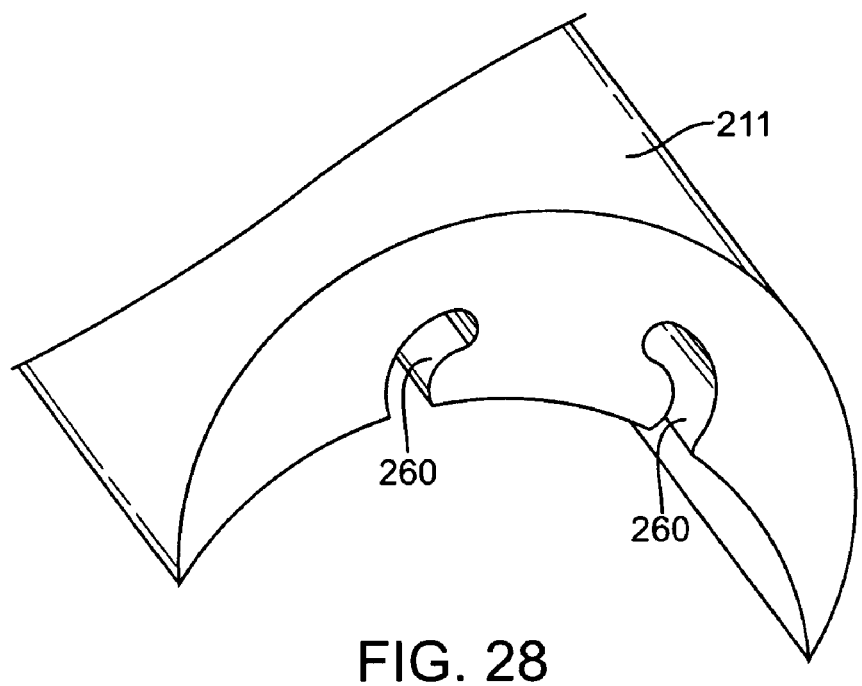
FIG. 28 is a cross-sectional perspective view of the seal cover of FIG. 26, particularly taken transversely to the axis of the seal cover.

The seal cover 211 is composed of a suitable electrically insulative material, such as, silicone or polyurethane. The seal cover 211 is shaped and sized in a manner that allows it to fit onto the receptacle 206 over the lever arms 220 of the electrical contacts 208. As best shown in FIGS. 26 and 27, the seal cover 211 includes a series of paired channels 260 that extend along its inner surface for respective receiving the pairs of lever arms 220 of the electrical contacts 208. In this manner, the interaction between the lever arms 220 and respective channels 260 will allow the seal cover 211 to be press fit onto the receptacle 206, and will further ensure electrical isolation between the electrical contacts 208. Preferably, the cross-sectional shape of the channels 260 through the thickness of the seal cover 211 matches the shape of the lever arms 220, as shown in FIG. 28. In the illustrated embodiment, the channels 260 match the curvature of the lever arms 220, thereby providing a secure fit between the seal cover 211 and the electrical contacts 208.

Figure 31:
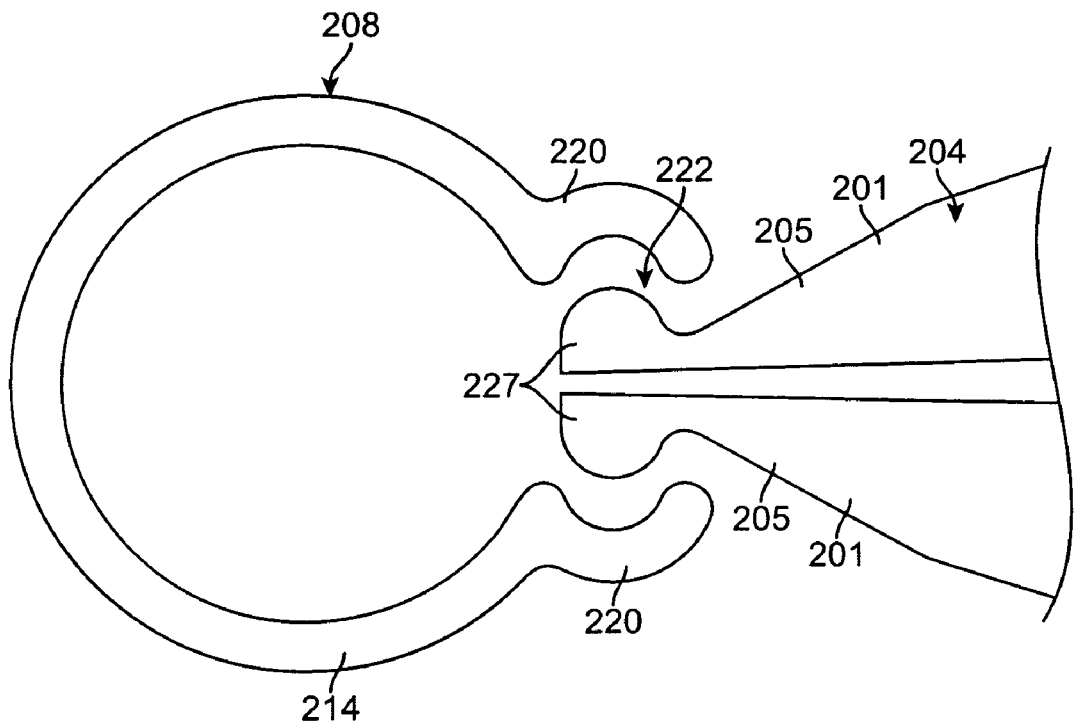
FIG. 31 is a side view of the electrical contact of FIG. 22, particularly showing the tool of FIG. 30 inserted within the tool passage of the electrical contact in a closed position.

As briefly discussed above, the proximal end of the electrical lead 102 may effortlessly be inserted into and withdrawn from the lead port 210 via mechanical interaction between the tool 204 and the lever arms 220 of the electrical contacts 208. In particular, while the tool 204 is in the closed position (which occurs naturally due to the spring force exerted between the pin 203 and the arms 201 of the tool 204), the mating elements 227 can be inserted into the tool passages 222 of the respective electrical contacts 208, as shown in FIG. 31. This can be accomplished by laterally placing the mating elements 227 into the tool passages 222 or axially threading the mating elements 227 along the tool passage 222 of each electrical contact 208 from the distal end to the proximal end of the connector 200 (i.e., engaging the distal-most electrical contact 208, than the next distal-most electrical contact 208, and so forth) or from the proximal end to the distal end of the connector 200 (i.e., engaging the proximal-most electrical contact 208, than the next proximal-most electrical contact 208, and so forth). Preferably, the tool 204 is wide enough, such that the mating elements 227 can simultaneously engage all of the electrical contacts 208.

Figure 32:
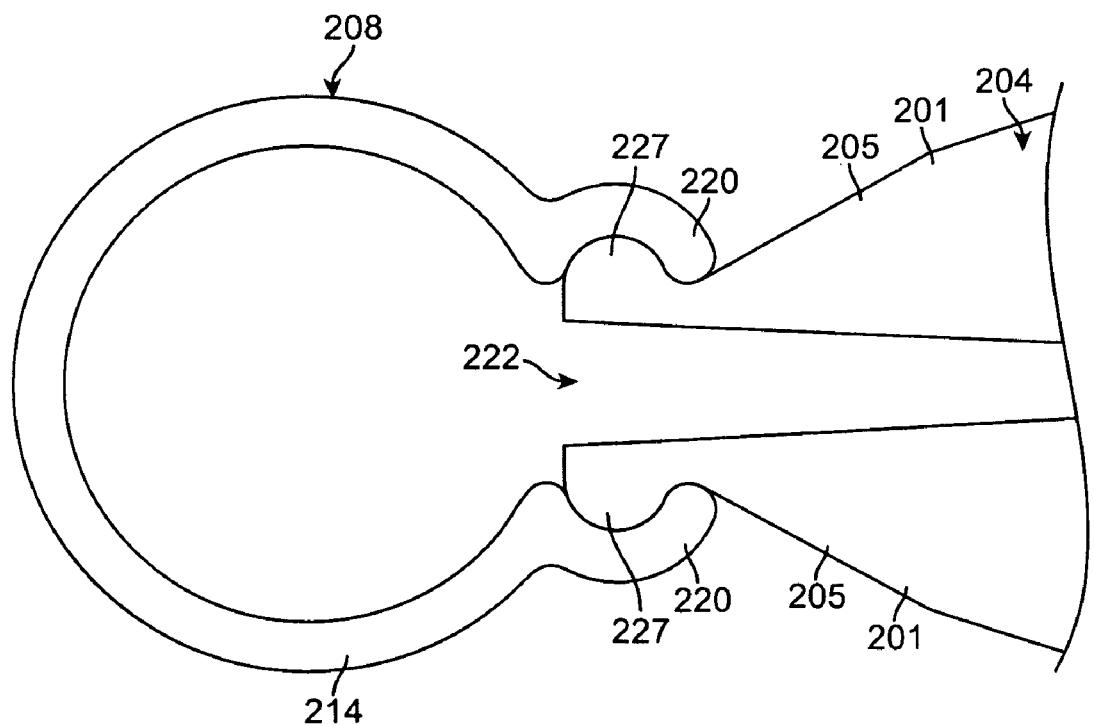
FIG. 32 is a side view of the electrical contact of FIG. 22, particularly showing the tool of FIG. 30 inserted within the tool passage of the electrical contact in an open position.

As shown in FIG. 32, the distal ends 205 of the tool arms 201, and thus the mating elements 227, can then be displaced away from each other by squeezing the proximal ends 207 of the tool arms 201 together to place the tool 204 into the open position, so that the mating elements 227 firmly engage the lever arms 220 of the electrical contacts 208. Once engaged with the lever arms 220, the mating elements 227 can be further displaced away from each other by further squeezing the proximal ends 207 of the tool arms 201, thereby placing the collar 214 of each electrical contact 208 into an expanded state (shown in phantom in FIG. 29), so that each of the lead passages 216 has a diameter slightly greater than the diameter of the electrical lead 102. As a result, the proximal end of the electrical lead 102, when inserted into the lead port 210, easily passes through the lead passages 216 of the respective electrical contacts 208 with a minimal amount of insertion force.

Figure 29:
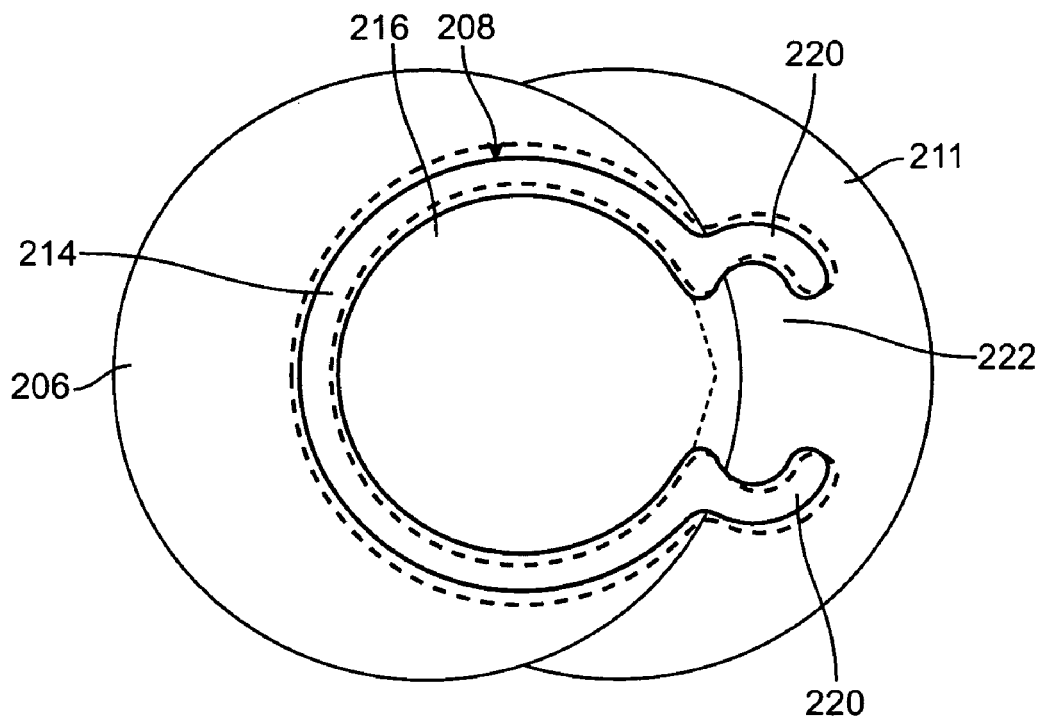
FIG. 29 is a cross-sectional view of the connector of FIG. 18, particularly taken transversely to the axis of the connector.

Once the electrical lead 102 is firmly engaged within the connector 200, the mating elements 227 can be displaced toward each other to place the tool 204 back in the closed state by releasing the proximal ends 207 of the tool arms 201, thereby allowing the spring force of the electrical contacts 108 to naturally urge each of the collars 114 into a contracted state (shown in FIG. 29). As result, the electrical contacts 208 firmly engage the respective terminals 118 of the electrical lead 102. The tool 204, while in the closed state, can then be removed from the connector 200.

Alternatively, if a pin is used as the tool 204, rather than using a seal cover 211 to cover the exposed lever arms 220 of the electrical contacts 208, the receptacle 206 may include a pin port (much like the pin port 112 illustrated in FIG. 5) through which the pin is inserted. In this case, the pin can be inserted through the pin port to displace the lever arms 220 of the electrical contacts 208 away from each other to place the collar 114 into the expanded state, thereby allowing the proximal end of the stimulation lead 102 to be inserted into the lead port 210. The pin can then be removed from the pin port to allow the spring force of the electrical contacts 208 to displace the lever arms 220 toward each other and place the collars 114 back into the contracted state, thereby firmly engaging the terminals 118 of the electrical lead 102

If the connector 200 is provided with a connector block 217, a torque wrench can be introduced through the securement opening 215 (shown in FIG. 18) to tighten the set screw down on the retention sleeve 105 of the electrical lead 102.

Although the connector 200 has been described as having electrical contacts 208 with lever arms 220 that are displaced away from each other using a tool to place the collars 214 of the contacts 208 within their expanded states, and displaced toward each other by removing the tool to place the collars 214 of the contacts 208 within their collapsed states, connectors that operate in an opposite manner can be used. For example, electrical contacts similar to the contacts 108 described above with respect to the connector 100 can be used. In this case, the contacts would be designed, such that their spring force naturally urges the collars of the contacts into a contract state that firmly engages the respective terminals 118 of the electrical lead 102. Thus, a tool, such as pliers, can be used to squeeze the lever arms together (i.e., displace the lever arms toward each other) to place the collars into their expanded states, and released from the lever arms to allow the spring force of the electrical contacts 108 to naturally urge the collars into their contracted states.

It should be appreciated that the previously described connectors 100, 200 and derivations thereof provide several advantages over the prior art connectors. For example, connectors 100, 200 obviate the need for expensive contacts by providing contacts that can be firmly engaged with the terminals of electrical leads using a tool or the natural spring force of the contacts. Also, these contacts have a relatively small profile compared to prior art contacts, and therefore minimize the profile of the resulting connectors 100, 200. The connectors 100, 200 are also relatively easy to assemble. The use of simple tools, such as the pin 104 or leverage tool 204, facilitates insertion of electrical leads within the connectors 100, 200 at a lower cost as compared to relatively expensive torque wrenches. The connectors 100, 200 provide these advantages while at the same time maintaining or improving upon the retention force and electrical reliability of prior art connectors.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable connector, comprising:
   an electrically insulative receptacle having a port configured for receiving an electrical lead body portion that carries an electrical terminal;
   an electrical spring clip contact mounted within the receptacle, the contact including a collar and opposing lever arms, the collar configured for being placed between an expanded state for receiving the terminal therein when the lead body portion is received within the port and a collapsed state for firmly engaging the terminal, the lever arms configured for being displaced using a tool to correspondingly place the collar between the expanded state and the collapsed state.

2. The implantable connector of claim 1, further comprising an electrical conductor connected to the contact.

3. The implantable connector of claim 1, wherein the contact has a spring force that urges the collar into the expanded state.

4. The implantable connector of claim 1, wherein the contact has a spring force that urges the collar into the collapsed state.

5. The implantable connector of claim 1, wherein the lever arms are configured for being displaced toward each other to correspondingly place the collar in the expanded state and for being displaced away each other to correspondingly place the collar in the collapsed state.

6. The implantable connector of claim 1, wherein the lever arms are configured for being displaced away from each other to correspondingly place the collar in the expanded state and for being displaced toward each other to correspondingly place the collar in the collapsed state.

7. The implantable connector of claim 1, wherein the electrical contact comprises a sheet of metal having first and second opposing edges, and wherein a first one of the lever arms extends from the first edge, a second one of the lever arms extends from the second edge, and the sheet of metal is wrapped around on itself, such that the lever arms oppose each other.

8. The implantable connector of claim 1, wherein the lever arms are axially offset from each other.

9. The implantable connector of claim 8, wherein the plurality of lever arms comprises two lever arms and a single lever arm opposing and axially interposed between the two lever arms.

10. The implantable connector of claim 1, wherein the receptacle has another port configured for receiving the tool.

11. The implantable connector of claim 1, wherein the lever arms are exposed outside of the receptacle, the implantable connector further comprising an electrically insulative cover configured for being interference fit over the lever arms.

12. The implantable connector of claim 1, wherein the port is configured for receiving an electrical lead body portion that carries a plurality of electrical terminals axially spaced along the lead body portion, the implantable connector comprising a plurality of electrical spring clip contacts axially mounted within the receptacle, each of the contacts including a collar and opposing lever arms, the collars configured for being placed between an expanded state for receiving the respective terminals therein when the lead body portion is received within the port and a collapsed state for firmly engaging the respective terminals, the lever arms configured for being displaced using a tool to correspondingly place the collars between the expanded state and the collapsed state.

13. An implantable lead assembly, comprising:
   a first electrical lead having a first lead body portion and an electrical terminal carried by the first lead body portion; and
   a second electrical lead having second lead body portion and a connector carried by the second lead body portion, the connector comprising an electrically insulative receptacle having a port configured for receiving the first lead body portion, and an electrical spring clip contact mounted within the receptacle, the contact including a collar and opposing lever arms, the collar configured for being placed between an expanded state for receiving the terminal therein when the first lead body portion is received within the port and a collapsed state to firmly engage the terminal, the lever arms configured for being displaced using a tool to correspondingly place the collar between the expanded state and the collapsed state.

14. The implantable lead assembly of claim 13, wherein the connector further comprises an electrical conductor connected to the contact and extending through the second lead body portion.

15. The implantable lead assembly of claim 13, wherein the contact has a spring force that urges the collar into the expanded state.

16. The implantable lead assembly of claim 13, wherein the contact has a spring force that urges the collar into the collapsed state.

17. The implantable lead assembly of claim 13, wherein the lever arms are configured for being displaced toward each other to correspondingly place the collar in the expanded state and for being displaced away each other to correspondingly place the collar in the collapsed state.

18. The implantable lead assembly of claim 13, wherein the lever arms are configured for being displaced away from each other to correspondingly place the collar in the expanded state and for being displaced toward each other to correspondingly place the collar in the collapsed state.

19. The implantable lead assembly of claim 13, wherein the electrical contact comprises a sheet of metal having first and second opposing edges, and wherein a first one of the lever arms extends from the first edge, a second one of the lever arms extends from the second edge, and the sheet of metal is wrapped around on itself, such that the lever arms oppose each other.

20. The implantable lead assembly of claim 13, wherein the lever arms are axially offset from each other.

21. The implantable lead assembly of claim 13, wherein the plurality of lever arms comprises two lever arms and a single lever arm opposing and axially interposed between the two lever arms.

22. The implantable lead assembly of claim 13, wherein the receptacle has another port configured for receiving the tool.

23. The implantable lead assembly of claim 13, wherein the lever arms are exposed outside of the receptacle, the connector further comprising an electrically insulative cover configured for being interference fit over the lever arms.

24. The implantable lead assembly of claim 13, wherein the first lead body portion is a proximal lead body portion, and the first electrical lead further comprises a distal lead body portion and an electrode carried by the distal lead body portion.

25. The implantable lead assembly of claim 13, wherein the first electrical lead has a plurality of electrical terminals axially spaced along the first lead body portion, the connector comprising a plurality of electrical spring clip contacts axially mounted within the receptacle, each of the electrical contacts including a collar and opposing lever arms, the collars configured for being placed between an expanded state for receiving the respective electrical terminals therein when the first lead body portion is received within the port and a collapsed state for firmly engaging the respective electrical terminals, the lever arms configured for being displaced using a tool to correspondingly place the collars between the expanded state and the collapsed state.

26. An implantable lead assembly kit, comprising:
an electrical lead comprising a lead body portion and an electrical terminal carried by the lead body portion;
a tool; and
a connector comprising an electrically insulative receptacle having a port configured for receiving the lead body portion, and an electrical spring clip contact mounted within the receptacle, the contact including a collar and opposing lever arms, the collar configured for being placed between an expanded state for receiving the terminal therein when the lead body portion is received within the port and a collapsed state to firmly engage the terminal, the lever arms configured for being displaced using a tool to correspondingly place the collar between the expanded state and the collapsed state.

27. The implantable lead assembly kit of claim 26, wherein the connector further comprises an electrical conductor connected to the contact.

28. The implantable lead assembly kit of claim 26, wherein the contact has a spring force that urges the collar into the expanded state.

29. The implantable lead assembly kit of claim 26, wherein the contact has a spring force that urges the collar into the collapsed state.

30. The implantable lead assembly kit of claim 26, wherein the lever arms are configured for being displaced toward each other to correspondingly place the collar in the expanded state and for being displaced away each other to correspondingly place the collar in the collapsed state.

31. The implantable lead assembly kit of claim 26, wherein the lever arms are configured for being displaced away from each other to correspondingly place the collar in the expanded state and for being displaced toward each other to correspondingly place the collar in the collapsed state.

32. The implantable lead assembly kit of claim 26, wherein the electrical contact comprises a sheet of metal having first and second opposing edges, and wherein a first one of the lever arms extends from the first edge, a second one of the lever arms extends from the second edge, and the sheet of metal is wrapped around on itself, such that the lever arms oppose each other.

33. The implantable lead assembly kit of claim 26, wherein the lever arms are axially offset from each other.

34. The implantable lead assembly kit of claim 26, wherein the plurality of lever arms comprises two lever arms and a single lever arm opposing and axially interposed between the two lever arms.

35. The implantable lead assembly kit of claim 26, wherein the receptacle has another port configured for receiving the tool.

36. The implantable lead assembly kit of claim 26, wherein the lever arms are exposed outside of the receptacle, the connector further comprising an electrically insulative cover configured for being interference fit over the lever arms.

37. The implantable lead assembly kit of claim 26, wherein the tool comprises a pin configured for being inserted between the lever arms to displace the lever arms away from each other.

38. The implantable lead assembly kit of claim 26, wherein the tool comprises a pair of tool arms configured for being placed between a closed state and inserted between the lever arms, and an open state to displace the lever arms away from each other.

39. The implantable lead assembly kit of claim 26, wherein the electrical lead has a plurality of electrical terminals axially spaced along the lead body portion, the connector comprising a plurality of electrical spring clip contacts axially mounted within the receptacle, each of the electrical contacts including a collar and opposing lever arms, the collars configured for being placed between an expanded state for receiving the respective electrical terminals therein when the lead body portion is received within the port and a collapsed state for firmly engaging the respective electrical terminals, the lever arms configured for being displaced using a tool to correspondingly place the collars between the expanded state and the collapsed state.

* * * * *